United States Patent [19]

Strunk et al.

[11] 4,260,552
[45] Apr. 7, 1981

[54] TETRASUBSTITUTED ORGANOTIN COMPOUNDS

[75] Inventors: Richard J. Strunk, Cheshire; Winchester L. Hubbard, Woodbridge; Robert E. Grahame, Jr., Cheshire, all of Conn.

[73] Assignee: Uniroyal, Inc., New York, N.Y.

[21] Appl. No.: 9,730

[22] Filed: Feb. 6, 1979

Related U.S. Application Data

[60] Division of Ser. No. 640,983, Dec. 15, 1975, which is a continuation-in-part of Ser. No. 536,678, Dec. 26, 1974.

[51] Int. Cl.$^3$ ............................................. C07E 7/22
[52] U.S. Cl. ................................. 260/429.7; 424/288
[58] Field of Search ....................................... 260/429.7

[56] References Cited

U.S. PATENT DOCUMENTS

| | | | |
|---|---|---|---|
| 2,604,483 | 7/1952 | Mack | 260/429.7 |
| 3,188,331 | 6/1965 | Weissenberger | 260/429.7 |
| 3,206,489 | 9/1965 | Stamm et al. | 260/429.7 |
| 3,256,253 | 6/1966 | Neumann et al. | 260/429.7 X |
| 3,365,479 | 1/1968 | Lefort | 260/429.7 |
| 3,398,169 | 8/1968 | Neumann et al. | 260/429.7 |
| 3,440,255 | 4/1969 | Matsuda et al. | 260/429.7 |
| 3,641,037 | 2/1972 | Bublitz | 260/429.7 X |
| 3,642,845 | 2/1972 | Ramsder | 260/429.7 |
| 3,723,089 | 3/1973 | Peterson | 260/429.7 |
| 3,725,446 | 4/1973 | Peterson | 260/429.7 |
| 3,784,580 | 1/1974 | Peterson | 260/429.7 |
| 3,850,970 | 11/1974 | Peterson et al. | 260/429.7 |
| 3,976,672 | 8/1976 | Strunk et al. | 260/429.7 |

FOREIGN PATENT DOCUMENTS

| | | | |
|---|---|---|---|
| 1212531 | 3/1966 | Fed. Rep. of Germany | 260/429.7 |
| 966813 | 8/1964 | United Kingdom | 260/429.7 |

OTHER PUBLICATIONS

Ayrey et al., J. Organometal, Chem. 35, 105–109, (1972).

*Primary Examiner*—Helen M. S. Sneed
*Attorney, Agent, or Firm*—Anthony Lagani, Jr.

[57] ABSTRACT

Tetrasubstituted organotin compounds, which are useful for controlling insects and other pests and which also exhibit herbicidal activity, are disclosed. Many of these organotin compounds are new compounds.

14 Claims, No Drawings

TETRASUBSTITUTED ORGANOTIN COMPOUNDS

This is a division of application Ser. No. 640,983, filed Dec. 15, 1975, which is a continuation-in-part of application Ser. No. 536,678, filed on Dec. 26, 1974.

RELATED CASE

The compounds in which X is —SO$_2$R$_1$ and in which R$_1$ is

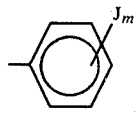

J being selected from the group consisting of linear and branched alkyl having 1 to 20 carbon atoms, cycloaliphatic having 4 to 6 carbon atoms and straight chain and branched alkenyl having 2 to 20 carbon atoms and m being an integer from 1 to 3, are claimed in copending application of Strunk and Hubbard, Ser. No. 641,060, filed Dec. 15, 1975, now U.S. Pat. No. 3,976,672.

This invention relates to tetrasubstituted organotin compounds which are useful for controlling insects and pests and as herbicides. Many of these tetrasubstituted organotins are new compounds

BACKGROUND OF THE INVENTION

Some tetrasubstituted organotin compounds are known from the prior art. For example, British Pat. No. 966,813 to Ziegler discloses a method for obtaining tetrasubstituted organotin compounds useful as high polymers, but no suggestion is made in this patent that these compounds might find utility in controlling insects and other pests or be useful as herbicides and fungicides.

Other substituted organotin compounds are also known from the prior art for use as pesticides, acaricides, bactericides, fungicides and herbicides or as protective coatings.

For example, U.S. Pat. No. 3,642,845 to Ramsden discloses bistrialkyltin compounds of the formula

wherein R is an alkyl group and R' is a hydrocarbon di-radical having a minimum of 8 carbon atoms. These compounds exhibit systemic pesticidal activity, particularly against lepidoptera insect larvae, such as the Southern army worm.

Another example is U.S. Pat. No. 3,206,489 to Stamm et al. which discloses tetrasubstituted tin compounds of the general formula

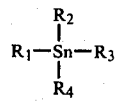

wherein R$_1$, R$_2$, R$_3$ and R$_4$ can be alkyl radicals having from 1 to 12 carbon atoms and an aromatic hydrocarbon radical provided one of the R substituents is an alkyl radical terminating in a lower aliphatic thioacid group which is characterized by the presence of a thiocarboxyl function. These compounds are indicated as being useful as herbicides.

A further example is U.S. Pat. No. 3,591,614 to Bublitz which discloses compounds of the formula

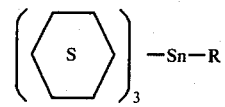

wherein R is 2-cyanoethyl, 2-carboxyethyl, or 2-carb-(lower)alkoxyethyl group. These substituted ethyl derivatives of tricyclohexyltin are indicated as being useful as acaricides for the control of mites and ticks.

An additional U.S. Pat. No. 3,641,037 to Bublitz discloses compounds of the formula

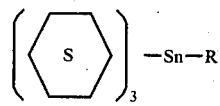

wherein R is 2-furyl, 2-pyridyl, 3-pyridyl, 1-indenyl, or 2-(2-pyridyl)ethyl, these compounds being useful as pesticides, particularly for the control of mites and ticks.

A further example is German Pat. No. 2,231,814 to Peterson which discloses compounds of the formula

wherein X is alkyl- or arylsulfonyl, alkyl- or arylthio or dialkylamino and R is alkyl of from 1 to 14 carbon atoms. These compounds are disclosed as being useful in protective coatings against bacteria, fungi, termites and barnacles.

Peterson, in U.S. Pat. No. 3,725,446, claims some of the same compounds, R-S-CH$_2$-Sn-R'$_3$, where R is alkyl of from 1 to 14 carbon atoms, aryl or substituted aryl, and R' is alkyl of 1 to 14 carbon atoms. These compounds are said to have pre-emergent and post-emergent herbicidal activity.

Another German Patent No. 2,106,040 (U.S. Pat. No. 3,784,580 to Peterson) also discloses compounds of the formula (R)$_3$SnCH$_2$-X wherein X is alkylsulfonyl, arylsulfonyl or dialkylsulfamoyl, the compounds being useful as pesticides and acaricides.

The compounds disclosed in the two German patents discussed immediately above differ from the compounds of this invention in that the "X" moiety is linked to the tin atom by a single methylene diradical instead of by a diradical having at least 2 carbon atoms.

Peterson has authored a paper, "Preparation and Reactions of some Sulfur-Substituted Tetraorganotin Compounds", J. Organometal Chem. 26, 215–223 (1971). The following paragraph appears at page 218:

"[(Phenylsulfonyl)methyl] tributyltin [(IV)] was found to be unreactive toward carbon dioxide and oxygen at room temperature, while exposure of a thin layer of (IV) to air resulted in ca. 50% decomposition to phenyl methyl sulfone and tributyltin oxide within four days. These findings, when regarded in conjunction, are in accord with hydrolysis being responsible for the air sensitivity of (IV)."

Peterson, in U.S. Pat. No. 3,794,670, has covered a method for preparing (organosulfonylmethyl) triorganotin compounds by reacting a triorganotin amine and an organosulfonylmethyl compound.

Ayrey et al. have published a paper, J. Organometal. Chem. 35, 105-109 (1972), in which they deal with the preparation of 3-(trialkylstannyl)propyl aryl sulfides, $R_3SnCH_2CH_2CH_2SR'$. No utility is stated for these compounds.

Koopmans, in U.S. Pat. No. 3,031,483, discloses compounds of the structure

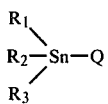

in which $R_1$, $R_2$ and $R_3$ may be the same or different and represent alkyl groups with 1-12 carbon atoms, phenyl groups or halophenyl groups, and Q represents one of a number of groups, including

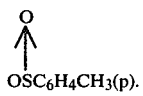

These compounds have fungicidal and bactericidal properties.

THE INVENTION

The novel organotin compounds of this invention are tetrasubstituted tin compounds having the general formula

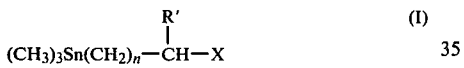

wherein:
R' is hydrogen, hydroxyl, methyl or ethoxy;
X is
- (a) —$SO_2R_1$, R' being hydrogen, and wherein $R_1$ is a straight chain or branched alkyl having 1 to 18 carbon atoms, cyclohexyl, benzyl, phenyl or phenyl substituted with one or more groups which may be the same or different and which may be alkoxy having 1 to 8 carbon atoms, phenoxy, alkylthio having 1 to 8 carbon atoms, halogen, nitro, acetyl, acetamido, carboxy, alkoxycarbonyl, carbamoyl, cyano, hydroxy, trifluoromethyl, benzyl, naphthyl or norbornyl; naphthyl, biphenylyl, piperidinoethylmethiodide, —$R_2Sn(CH_3)_3$ wherein $R_2$ is polymethylene having from 2 to 11 carbon atoms, —$R_4SO_2R_5Sn(CH_3)_3$ wherein $R_4$ is ethylene and $R_5$ is as defined for $R_2$ above;
- (b) —$OR_7$, R' being hydrogen, and wherein $R_7$ is a straight chain or branched alkyl having 8 to 16 carbon atoms, aryl, alkoxyaryl, alkaryl, haloaryl, N,N-dialkylaminoalkyl, —$R_8Sn(CH_3)_3$ wherein $R_8$ is alkylene having 2 to 11 carbon atoms, cycloaliphatic having 4 to 6 carbon atoms, tetrahydro-1,1-dioxo-3-thienyl;
- (c) —$SR_{10}$, R' being hydrogen, and wherein $R_{10}$ is a straight chain or branched alkyl having 1 to 16 carbon atoms, phenyl, chlorophenyl, t-butylphenyl or —$R_2Sn(CH_3)_3$;
- (d) —$COR_{11}$, R' being hydrogen, and wherein $R_{11}$ is —$NHR_{12}$ wherein $R_{12}$ is a straight chain or branched alkyl having 1 to 12 carbon atoms or aryl; —$NHCH_2OH$; —$NHNH_2$; —$NHCH_2NHCOR_2Sn(CH_3)_3$; —$OR_{13}$ wherein $R_{13}$ is a straight chain or branched alkyl having 8 to 15 carbon atoms; —$(CH_2)_mOH$, wherein m is an integer from 2 to 4; —$(CH_2)_pN(R_{14})_2$ wherein p is an integer from 2 to 4 and $R_{14}$ is a straight chain or branched alkyl having 1 to 5 carbon atoms; —$(CH_2)_qOCOR_2Sn(CH_3)_3$ wherein q is as defined for p above; —$(CH_2)_sN^{\oplus}(CH_3)_3I^{\ominus}$ wherein s is as defined for p above;
- (e) —$NHCONH_2$, R' being hydrogen;
- (f) —$NHCSNH_2$, R' being hydrogen;
- (g) 1-imidazolyl, R' being hydrogen;
- (h) N-2-oxopyrrolidinyl, R' being hydrogen;
- (i) —$OCOR_{17}$, R' being hydrogen, and wherein $R_{17}$ is —$NHR_{18}$ wherein $R_{18}$ is a straight chain or branched alkyl having 1 to 5 carbon atoms; 2-furyl; and —$O(CH_2)_tSn(CH_3)_3$ wherein t is from 2 to 11;
- (j) —$PO(OR_{20})_2$, R' being hydrogen or ethoxy, and wherein $R_{20}$ is a straight chain or branched alkyl having 1 to 5 carbon atoms;
- (k) tetrahydro-1,1-dioxo-2-thenyl, R' being hydroxyl;
- (l) —$Si(OR_{21})_3$, R' being hydrogen, and wherein $R_{21}$ is a straight chain or branched alkyl having 1 to 5 carbon atoms;

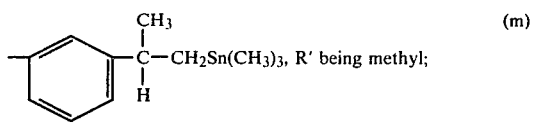

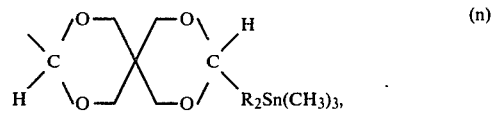

R' being hydrogen;
- (o) 2-pyridyl;
- (p) 4-pyridyl;
- (q) 2-alkyl-5-pyridyl; and n is an integer from 1 to 10.

The term "aryl", as employed above and as used throughout the application and in the appended claims, is intended to be inclusive of and should be understood as being inclusive of phenyl and substituted phenyl, e.g., phenyl substituted with halogen(s) or alkyl group(s) having 1-4 carbon atoms. X can also be

wherein $R_{28}$ is a straight chain or branched alkyl having 1 to 18 carbon atoms, cyclohexyl, benzyl, phenyl, t-butylphenyl or chlorophenyl.

When X is —$SO_2R_1$, a preferred group of compounds is that in which $R_1$ is a straight chain or branched alkyl having 1 to 18 carbon atoms, cyclopentyl, cyclohexyl, benzyl, phenyl, alkoxyphenyl having 1 to 3 carbon atoms in the alkoxy group, phenoxyphenyl, bicyclo[2.2.1]heptylphenyl, halophenyl, piperidinoethylmethiodide, —$R_2Sn(CH_3)_3$ wherein $R_2$ is polymethylene having from 2 to 11 carbon atoms or —$R_4SO_2R_5Sn(CH_3)_3$ wherein $R_4$ is ethylene and $R_5$ is as defined for $R_2$ above.

These and the other organotin compounds of this invention have been found to exhibit a wide variety of activities. For example, they have been found useful as insecticides, acaricides and herbicides.

The compounds having these and related utilities are tetrasubstituted tin compounds having the general formula

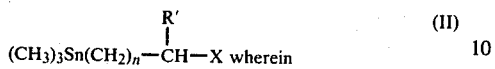

R' is hydrogen, hydroxyl, alkoxyl or a straight chain or branched alkyl group having 1 to 5 carbon atoms;

X is (a) $-SO_2R_1$, R' being hydrogen, and wherein $R_1$ is a straight chain or branched alkyl having 1 to 18 carbon atoms, cyclohexyl, benzyl, phenyl or phenyl substituted with one or more groups which may be the same or different and which may be linear or branched alkyl having 1 to 20 carbon atoms, cycloaliphatic having 4 to 6 carbon atoms, straight chain or branched alkenyl having 2 to 20 carbon atoms, alkoxy having 1 to 8 carbon atoms, phenoxy, alkylthio having 1 to 8 carbon atoms, halogen, nitro, acetyl, acetamido, carboxy, alkoxycarbonyl, carbamoyl, cyano, hydroxy, trifluoromethyl, benzyl, naphthyl or norbornyl; naphthyl, biphenylyl, piperidinoethylmethiodide, $-R_2Sn(CH_3)_3$ wherein $R_2$ is polymethylene having from 2 to 11 carbon atoms, $-R_4SO_2R_5Sn(CH_3)_3$ wherein $R_4$ is ethylene and $R_5$ is as defined for $R_2$ above;

(b) $-OR_7$, wherein $R_7$ is a straight chain or branched alkyl having 1 to 20 carbon atoms, haloalkyl, aryl, haloaryl, alkaryl, alkoxyaryl, epoxyalkylene wherein the alkylene group has 2 to 4 carbon atoms, N,N-dialkylaminoalkyl, tetrahydro-1,1-dioxo-3-thienyl, $-R_8Sn(CH_3)_3$ wherein $R_8$ is alkylene having 2 to 11 carbon atoms, cycloaliphatic having 4 to 6 carbon atoms or aryl;

(c) $-SR_{10}$, R' being hydrogen, and wherein $R_{10}$ is a straight chain or branched alkyl having 1 to 18 carbon atoms, cyclohexyl, benzyl, phenyl or phenyl substituted with one or more groups which may be the same or different and which may be linear or branched alkyl having 1 to 20 carbon atoms, cycloaliphatic having 4 to 6 carbon atoms, straight chain or branched alkenyl having 2 to 20 carbon atoms, alkoxy having 1 to 8 carbon atoms, alkylthio having 1 to 8 carbon atoms, halogen, nitro, acetyl, acetamido, carboxy, alkoxycarbonyl, carbamoyl, cyano, hydroxy, trifluoromethyl, benzyl, naphthyl or norbornyl; naphthyl, biphenylyl, piperidinoethylmethiodide, $-R_2Sn(CH_3)_3$ wherein $R_2$ is polymethylene having from 2 to 11 carbon atoms, $-R_4SO_2R_5Sn(CH_3)_3$ wherein $R_4$ is ethylene and $R_5$ is as defined for $R_2$ above;

(d) $-COR_{11}$, wherein $R_{11}$ is $-NH_2$, $-NHNH_2$, $-NHCH_2OH$, $-NHR_{12}$ wherein $R_{12}$ is a straight chain or branched alkyl having 1 to 12 carbon atoms or aryl; $-NHCH_2NHCOR_2Sn(CH_3)_3$, $-OR_{13}$ wherein $R_{13}$ is a straight chain or branched alkyl having 1 to 15 carbon atoms, $-(CH_2)_mOH$ wherein m is an integer from 2 to 4, $-(CH_2)_pN(R_{14})_2$ wherein p is an integer from 2 to 4 and $R_{14}$ is a straight chain or branched alkyl having 1 to 5 carbon atoms, $-(CH_2)_qOCOR_2Sn(CH_3)_3$ wherein q is as defined for p above, $-(CH_2)_sN^{\oplus}(CH_3)_3I^{\ominus}$ wherein s is as defined for p above;

(e) $-NHCONH_2$;

(f) $-NHCSNH_2$;

(g) 2-pyridyl;

(h) 4-pyridyl;

(i) 2-alkyl-5-pyridyl;

(j) 9-carbazolyl;

(k) 1-imidazolyl;

(l) N-2-oxopyrrolidinyl;

(m) $-OCOR_{17}$, wherein $R_{17}$ is $-NHR_{18}$ wherein $R_{18}$ is a straight chain or branched alkyl having 1 to 5 carbon atoms or aryl; 2-furyl; and $-O(CH_2)_tSn(CH_3)_3$ wherein t is an integer from 2 to 11;

(n) $-PO(OR_{20})_2$ wherein $R_{20}$ is a straight chain or branched alkyl having 1 to 5 carbon atoms;

(o) tetrahydro-1,1-dioxo-2-thenyl;

(p) $-Si(OR_{21})_3$ wherein $R_{21}$ is a straight chain or branched alkyl having 1 to 5 carbon atoms;

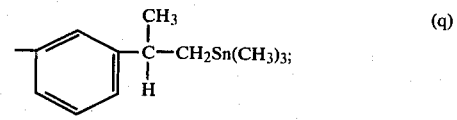

(r) cyano;

(s) OH;

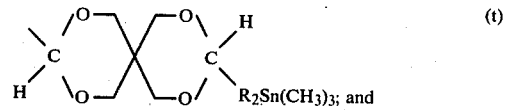

n is an integer from 1 to 10.

We recognize that the insecticidal, acaricidal and herbicidal activities of the compounds of the invention are derived from the trimethyltin segment of the molecule, i.e., $(CH_3)_3Sn-$. The degree and nature of activity of these compounds are also affected by that portion of the molecule that contains the

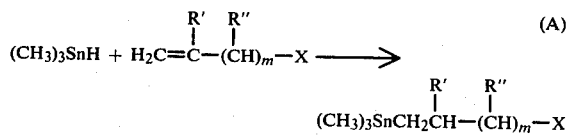

radical as, for example, phytotoxicity to beneficial plants, herbicidal activity to noxious plants, uptake and translocation in plants, retention in the soil, oral and/or dermal mammalian toxicity, control of physical properties such as volatility and solubility, hydrolytic and/or oxidative stability, sensitivity to solar ultraviolet, ease of entry into the food chain, degradation by microorganisms and/or higher forms of life, and practical formulation and useful application rate.

In general, the compounds of the invention can be obtained according to the one-step reaction process described by R. Sommer and H. G. Kuivila, *J. Org. Chem.*, 33, 802 (1968), which involves reacting a compound containing an olefinic moiety with trimethyltin hydride, according to the following scheme:

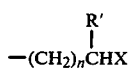

wherein X is as defined above, R' may be hydrogen, a straight chain or branched alkyl group having 1 to 5 carbon atoms or an alkoxy group having 1 to 5 carbon atoms, and R" may be hydrogen, hydroxyl, or an alkyl group having 1 to 5 carbon atoms, and m is an integer from 0 to 9.

In this synthesis, the substituted olefinic compounds and an equivalent amount of the organotin hydride are placed in a conventional glass reaction vessel under an inert atmosphere in the presence of a suitable solvent, where desired or as required, and with adequate stirring. The reaction mixture is irradiated by a mercury vapor lamp until no more organotin hydride is present, which is determined by infra-red spectrum analysis noting the absence of additional Sn-H absorption. The time for this to occur will vary depending upon the particular substituted olefinic compound used but will generally be about 4 to 48 hours, but, when n is 3 or higher, can be as long as 232 hours. The reaction mixture is normally maintained at a temperature of about 0° to 50° C. In cases where the reactants are heterogeneous and/or when the starting material is a solid, ether solvents such as diethyl ether and tetrahydrofuran, aromatic solvents such as benzene and toluene, esters and nitriles such as ethyl acetate and acetonitrile, alcohols such as methanol and ethanol, amides such as dimethylformamide, and the like, may be used to facilitate mixing of the reactants.

One mole of an unsaturated sulfone, formed by the addition of one mole of the organotin hydride to one mole of a sulfone containing two unsaturated (—C=C—) groups, for example a divinyl sulfone, may be reacted further according to (A) above with reagents such as mercaptans, amines, alcohols and phenols. The following equations in which the starting sulfone is divinyl sulfone, as in Example 3 hereinbelow, illustrate this aspect of the invention:

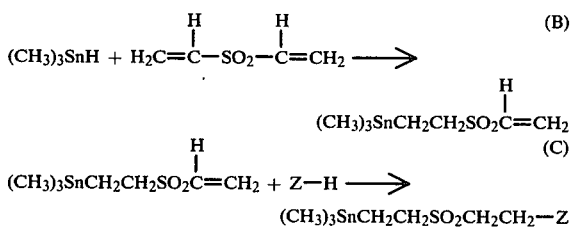

where Z may be $(CH_3)_3Sn-$, $(R_{24})_3Si-$, $(R_{25})_2N-$, $R_{26}S-$ or a $R_{27}O-$ group; $R_{24}$, $R_{25}$, $R_{26}$ and $R_{27}$ may be a straight chain or branched alkyl group having 1 to 5 carbon atoms, or an aryl group.

Employing the same general method described above for obtaining the organotin compound of (A), two equivalents of the organotin hydride can be reacted to form an adduct containing two organotin moieties according to the following equation:

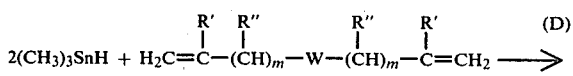

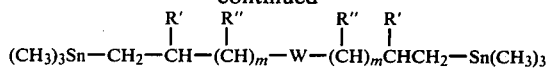

wherein R', R" and m are defined as above. W may be a sulfonyl diradical (—SO₂—) as in compounds 1 and 2 in Table I hereinbelow, a 1,2-ethylenedisulfonyl diradical (—SO₂—CH₂—CH₂—SO₂—) as in compound 17 in Table I hereinbelow, an oxy diradical (—O—) as in compounds 25 and 26 in Table I hereinbelow, a thio diradical (—S—) as in compound 36 in Table I hereinbelow, an N,N'-methylenebiscarbamoyl diradical

as in compound 41 in Table I hereinbelow, a 1,2-ethylenedioxydicarbonyl diradical

as in compound 45 in Table I hereinbelow, a carbonyldioxy diradical

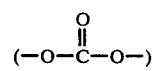

as in compound 52 in Table I hereinbelow, a phenylene diradical

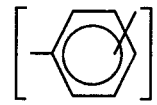

as in compound 60 in Table I hereinbelow, and a 2,4,8,10-tetraoxaspiro[5.5]undec-3,9-ylene diradical having the structure:

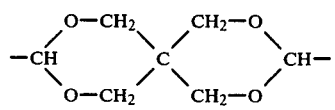

as in compound 63 in Table I hereinbelow. The preparative method is the same as that described for scheme (A) above except that two equivalents of the organotin hydride are required when the other reactant contains two olefinic moieties.

Where desired, purification of the organotin compounds can be achieved by using standard distillation, column chromatography, or recrystallization techniques.

Alternatively, the compounds of this invention can be made by the method of British Pat. No. 966,813 to Karl Ziegler using conventional free radical generators such as azobisisobutyronitrile, azotriphenylmethane and the like.

Thus, a wide variety of substituted olefinic compounds can be used to prepared the compounds of this invention. Examples of such compounds are listed below and grouped according to their primary function. In addition, the compound numbers in which specific compounds from the list were used to make the representative number of the compounds of this invention are also shown, these compounds being more fully identified in Table I hereinbelow.

|  | Compound No. |
|---|---|
| 1. Sulfones |  |
| divinyl sulfone | 1, 2, 16 |
| methyl vinyl sulfone; | 3 |
| ethyl vinyl sulfone; | 4 |
| n-propyl vinyl sulfone; |  |
| isopropyl vinyl sulfone; | 5 |
| n-butyl vinyl sulfone; |  |
| sec-butyl vinyl sulfone; | 6 |
| tert-butyl vinyl sulfone; |  |
| n-pentyl vinyl sulfone; |  |
| isopentyl vinyl sulfone; |  |
| sec-pentyl vinyl sulfone; |  |
| tert-pentyl vinyl sulfone; | 7 |
| n-hexyl vinyl sulfone; |  |
| cyclohexyl vinyl sulfone; | 11 |
| 4-methylcyclohexyl vinyl sulfone; |  |
| methallyl vinyl sulfone; |  |
| n-octyl vinyl sulfone; | 8 |
| tert-octyl vinyl sulfone; |  |
| benzyl vinyl sulfone; | 12 |
| 4-chlorobenzyl vinyl sulfone; |  |
| phenyl vinyl sulfone; | 13 |
| p-tolyl vinyl sulfone; | 66 |
| o-ethylphenyl vinyl sulfone; |  |
| p-ethylphenyl vinyl sulfone; | 67 |
| p-n-propylphenyl vinyl sulfone; |  |
| p-i-propylphenyl vinyl sulfone; | 68 |
| p-n-butylphenyl vinyl sulfone; |  |
| p-s-butylphenyl vinyl sulfone; |  |
| p-t-butylphenyl vinyl sulfone; | 14 |
| p-i-butylphenyl vinyl sulfone; |  |
| p-n-amylphenyl vinyl sulfone; | 69 |
| p-t-amylphenyl vinyl sulfone; | 70 |
| p-n-hexylphenyl vinyl sulfone; |  |
| p-n-heptylphenyl vinyl sulfone; |  |
| p-n-octylphenyl vinyl sulfone; | 71 |
| p-t-octylphenyl vinyl sulfone; |  |
| p-nonylphenyl vinyl sulfone; |  |
| p-decylphenyl vinyl sulfone; |  |
| p-dodecylphenyl vinyl sulfone; | 72 |
| p-n-dodecylphenyl vinyl sulfone; | 73 |
| p-tridecylphenyl vinyl sulfone; | 74 |
| p-cyclopentylphenyl vinyl sulfone; | 79 |
| p-cyclohexyl phenyl vinyl sulfone; | 80 |
| p-bicyclo[2.2.1]-hept-2-ylphenyl vinyl sulfone; | 81 |
| 3,4-dimethylphenyl vinyl sulfone; |  |
| 2,4-dimethylphenyl vinyl sulfone; | 75 |
| 2,5-dimethylphenyl vinyl sulfone; | 76 |
| 2,4-diethylphenyl vinyl sulfone; | 77 |
| 2,5-diethylphenyl vinyl sulfone; |  |
| 2,4-diisopropylphenyl vinyl sulfone; |  |
| 2,5-diisopropylphenyl vinyl sulfone; | 78 |
| 2,5-di-t-butylphenyl vinyl sulfone; |  |
| 2,5-dicyclohexylphenyl vinyl sulfone; |  |
| 2,4,6-trimethylphenyl vinyl sulfone; |  |
| 2,4,6-triethylphenyl vinyl sulfone; |  |
| 2,4,6-triisopropylphenyl vinyl sulfone; |  |
| 2,3,5,6-tetramethylphenyl vinyl sulfone; |  |
| 2,3,4,5,6-pentamethylphenyl vinyl sulfone; |  |
| p-allylphenyl vinyl sulfone; |  |
| p-propenylphenyl vinyl sulfone; |  |
| p-crotylphenyl vinyl sulfone; |  |
| p-methallylphenyl vinyl sulfone; |  |
| p-4-pentenylphenyl vinyl sulfone; |  |
| p-3-methylcrotylphenyl vinyl sulfone; |  |
| p-oleylphenyl vinyl sulfone; |  |
| p-methoxyphenyl vinyl sulfone; | 82 |
| p-ethoxyphenyl vinyl sulfone; |  |
| p-butoxyphenyl vinyl sulfone; |  |
| p-octoxyphenyl vinyl sulfone; |  |
| 2,4-dimethoxyphenyl vinyl sulfone; |  |
| 2,5-dimethoxyphenyl vinyl sulfone; |  |
| 3,4-dimethoxyphenyl vinyl sulfone; |  |

-continued

|  | Compound No. |
|---|---|
| p-methylthiophenyl vinyl sulfone; |  |
| p-butylthiophenyl vinyl sulfone; |  |
| p-octylthiophenyl vinyl sulfone; |  |
| 5-chloro-2-methoxyphenyl vinyl sulfone; |  |
| 2-chloro-4-methoxyphenyl vinyl sulfone; |  |
| 3-chloro-4-methoxyphenyl vinyl sulfone; |  |
| 5-bromo-2-methoxyphenyl vinyl sulfone; |  |
| 2-bromo-4-methoxyphenyl vinyl sulfone; |  |
| 3-bromo-4-methoxyphenyl vinyl sulfone; |  |
| 3-acetamido-4-methoxyphenyl vinyl sulfone; |  |
| 5-acetamido-2-methoxyphenyl vinyl sulfone; |  |
| 5-nitro-2-methoxyphenyl vinyl sulfone; |  |
| 2-nitro-4-methoxyphenyl vinyl sulfone; |  |
| 3-nitro-4-methoxyphenyl vinyl sulfone; |  |
| 2-methyl-4-methoxyphenyl vinyl sulfone; |  |
| 2-methyl-5-methoxyphenyl vinyl sulfone; |  |
| 2-methyl-5-chlorophenyl vinyl sulfone; |  |
| 2-methyl-5-bromophenyl vinyl sulfone; |  |
| p-fluorophenyl vinyl sulfone; | 84 |
| p-bromophenyl vinyl sulfone; | 83 |
| p-chlorophenyl vinyl sulfone; | 15 |
| 2,5-dichlorophenyl vinyl sulfone; |  |
| 3,4-dichlorophenyl vinyl sulfone; | 85 |
| 2,4,5-trichlorophenyl vinyl sulfone; |  |
| trifluoromethylphenyl vinyl sulfone; |  |
| 4-chloro-3-nitrophenyl vinyl sulfone; |  |
| 3-nitrophenyl vinyl sulfone; |  |
| 2-nitrophenyl vinyl sulfone; |  |
| 3,5-dichloro-2-hydroxyphenyl vinyl sulfone; |  |
| p-acetamidophenyl vinyl sulfone; |  |
| p-carboxyphenyl vinyl sulfone; |  |
| p-alkoxycarbonylphenyl vinyl sulfone; |  |
| p-carbamoylphenyl vinyl sulfone; |  |
| p-cyanophenyl vinyl sulfone; |  |
| p-acetylphenyl vinyl sulfone; |  |
| 2-naphthyl vinyl sulfone; | 86 |
| 4-biphenylyl vinyl sulfone; |  |
| n-dodecyl vinyl sulfone; | 9 |
| n-octadecyl vinyl sulfone; | 10 |
| 1,2-ethylenebis(vinyl sulfone); | 17 |
| 1-ethyl-1,2-ethylenebis(vinyl sulfone); |  |
| 1,4-tetramethylenebis(vinyl sulfone); |  |
| 1,6-hexamethylenebis(vinyl sulfone); |  |
| 1,8-octamethylenebis(vinyl sulfone); |  |
| 2,2-propylidenebis(vinyl sulfone); |  |
| 1,1'-methylenebismethyl vinyl sulfone; |  |
| 2-(trimethylstannyl)ethyl vinyl sulfone; |  |
| methyl 3-butenyl sulfone; |  |
| ethyl 4-pentenyl sulfone; |  |
| n-propyl 5-hexenyl sulfone; |  |
| isopropyl 6-heptenyl sulfone; |  |
| n-butyl 7-octenyl sulfone; |  |
| sec-butyl 8-nonenyl sulfone; |  |
| tert-butyl 9-decenyl sulfone; |  |
| n-pentyl 10-undecenyl sulfone; |  |
| isopentyl 3-butenyl sulfone; |  |
| sec-pentyl 4-pentenyl sulfone; |  |
| tert-pentyl 5-hexenyl sulfone; |  |
| n-hexyl 6-heptenyl sulfone; |  |
| cyclohexyl 7-octenyl sulfone; |  |
| 4-methylcyclohexyl 8-nonenyl sulfone; |  |
| methallyl 9-decenyl sulfone; |  |
| n-octyl 10-undecenyl sulfone; |  |
| tert-octyl 3-butenyl sulfone; |  |
| benzyl 4-pentenyl sulfone; |  |
| 4-chlorobenzyl 5-hexenyl sulfone; |  |
| 6-hexenyl phenyl sulfone; |  |
| 3-butenyl p-tolyl sulfone; |  |
| 3-butenyl p-t-butylphenyl sulfone; | 87 |
| 4-pentenyl p-ethylphenyl sulfone; |  |
| 5-hexenyl p-tolylphenyl sulfone; | 88 |
| 6-heptenyl p-n-propylphenyl sulfone; |  |
| 7-octanenyl p-i-propylphenyl sulfone; |  |
| 8-nonenyl p-n-butylphenyl sulfone; |  |
| 9-decenyl p-s-butylphenyl sulfone; |  |
| 10-undecenyl p-tolyl sulfone; | 89 |
| 4-pentenyl p-i-butylphenyl sulfone; |  |
| 5-hexenyl p-n-amylphenyl sulfone; |  |
| 6-heptenyl t-amylphenyl sulfone; |  |

11
-continued

| | Compound No. |
|---|---|
| 7-octenyl p-n-hexylphenyl sulfone; | |
| 8-nonenyl p-n-heptylphenyl sulfone; | |
| 9-decenyl p-octylphenyl sulfone; | |
| 10-undecenyl t-octylphenyl sulfone; | |
| 3-butenyl p-nonylphenyl sulfone; | |
| 4-pentenyl p-decylphenyl sulfone; | |
| 5-hexenyl p-n-dodecylphenyl sulfone; | |
| 6-heptenyl p-dodecylphenyl sulfone; | |
| 7-octenyl p-tridecylphenyl sulfone; | |
| 8-nonenyl p-cyclopentylphenyl sulfone; | |
| 9-decenyl p-cyclohexylphenyl sulfone; | |
| 10-undecenyl bicyclo[2.2.1]hept-2-ylphenyl sulfone; | |
| 3-butenyl 3,4-dimethylphenyl sulfone; | |
| 4-pentenyl 2,4-dimethylphenyl sulfone; | |
| 5-hexenyl 2,5-dimethylphenyl sulfone; | |
| 6-heptenyl 2,4-diethylphenyl sulfone; | |
| 7-octenyl 2,5-diethylphenyl sulfone; | |
| 8-nonenyl 2,4-diisopropylphenyl sulfone; | |
| 9-decenyl 2,5-diisopropylphenyl sulfone; | |
| 10-undecenyl 2,5-di-t-butylphenyl sulfone; | |
| 3-butenyl dicyclohexylphenyl sulfone; | |
| 4-pentenyl 2,4,6-trimethylphenyl sulfone; | |
| 5-hexenyl 2,4,6-triethylphenyl sulfone; | |
| 6-heptenyl 2,4,6-triisopropylphenyl sulfone; | |
| 7-octenyl 2,3,5,6-tetramethylphenyl sulfone; | |
| 8-nonenyl 2,3,4,5,6-pentamethylphenyl sulfone; | |
| 9-decenyl p-methoxyphenyl sulfone; | |
| 10-undecenyl p-ethoxyphenyl sulfone; | |
| 3-butenyl p-butoxyphenyl sulfone; | |
| 4-pentenyl p-octoxyphenyl sulfone; | |
| 5-hexenyl 2,4-dimethoxyphenyl sulfone; | |
| 6-heptenyl 2,5-dimethoxyphenyl sulfone; | |
| 7-octenyl 3,4-dimethoxyphenyl sulfone; | |
| 8-nonenyl p-methylthiophenyl sulfone; | |
| 9-decenyl p-butylthiophenyl sulfone; | |
| 10-undecenyl p-octylthiophenyl sulfone; | |
| 3-butenyl 5-chloro-2-methoxyphenyl sulfone; | |
| 4-pentenyl 2-chloro-4-methoxyphenyl sulfone; | |
| 5-hexenyl 3-chloro-4-methoxyphenyl sulfone; | |
| 6-heptenyl 5-bromo-2-methoxyphenyl sulfone; | |
| 7-octenyl 2-bromo-4-methoxyphenyl sulfone; | |
| 8-nonenyl 3-bromo-4-methoxyphenyl sulfone; | |
| 9-decenyl 3-acetamido-4-methoxyphenyl sulfone; | |
| 10-undecenyl 5-acetamido-2-methoxyphenyl sulfone; | |
| 3-butenyl 2-nitro-4-methoxyphenyl sulfone; | |
| 4-pentenyl 3-nitro-4-methoxyphenyl sulfone; | |
| 5-hexenyl 2-methyl-4-methoxyphenyl sulfone; | |
| 6-heptenyl 2-methyl-5-methoxyphenyl sulfone; | |
| 7-octenyl 2-methyl-5-chlorophenyl sulfone; | |
| 8-nonenyl 2-methyl-5-bromophenyl sulfone; | |
| 9-decenyl p-fluorophenyl sulfone; | |
| 10-undecenyl p-bromophenyl sulfone; | |
| 3-butenyl p-chlorophenyl sulfone; | |
| 4-pentenyl 2,5-dichlorophenyl sulfone; | |
| 5-hexenyl 3,4-dichlorophenyl sulfone; | |
| 6-heptenyl 2,4,5-trichlorophenyl sulfone; | |
| 7-octenyl trifluoromethylphenyl sulfone; | |
| 8-nonenyl 4-chloro-3-nitrophenyl sulfone; | |
| 9-decenyl 3-nitrophenyl sulfone; | |
| 10-undecenyl 2-nitrophenyl sulfone; | |
| 3-butenyl 3,5-dichloro-2-hydroxyphenyl sulfone; | |
| 4-pentenyl p-acetamidophenyl sulfone; | |
| 5-hexenyl p-carboxyphenyl sulfone; | |
| 6-heptenyl alkoxycarbonylphenyl sulfone; | |
| 7-octenyl carbamoylphenyl sulfone; | |
| 8-nonenyl cyanophenyl sulfone; | |
| 9-decenyl p-acetylphenyl sulfone; | |
| 10-undecenyl 2-naphthyl sulfone; | |
| 3-butenyl 4-biphenylyl sulfone; | |
| 4-pentenyl n-dodecyl sulfone; | |
| 5-hexenyl n-octadecyl sulfone. | |

2. Ethers

| | Compound No. |
|---|---|
| divinyl ether; | 25 |
| ethyl vinyl ether; | 18 |
| n-propyl vinyl ether; | |
| isopropyl vinyl ether; | |
| n-butyl vinyl ether; | 19 |

12
-continued

| | Compound No. |
|---|---|
| isobutyl vinyl ether; | 20 |
| n-pentyl vinyl ether; | |
| n-hexyl vinyl ether; | |
| cyclohexyl vinyl ether; | |
| n-octyl vinyl ether; | |
| isooctyl vinyl ether; | 21 |
| n-decyl vinyl ether; | 22 |
| n-dodecyl vinyl ether; | 23 |
| hexadecyl vinyl ether; | 33 |
| benzyl vinyl ether; | |
| 2,2,2-trifluoroethyl vinyl ether; | 31 |
| phenyl vinyl ether; | |
| p-chlorophenyl vinyl ether; | |
| o-tolyl vinyl ether; | |
| p-methoxyphenyl vinyl ether; | |
| 2,6,8-trimethyl-4-nonyl vinyl ether; | 65 |
| N,N-dimethylaminoethyl vinyl ether; | 32 |
| diallyl ether; | 26 |
| allyl glycidyl ether; | 24 |
| allyl phenyl ether; | 27 |
| allyl p-tert-butylphenyl ether; | 28 |
| allyl p-methoxyphenyl ether; | 29 |
| allyl p-chlorophenyl ether; | 30 |
| allyl (tetrahydro-1,1-dioxo-3-thienyl)ether; | 34 |
| 1,4-divinyloxybutane; | |
| 3-vinyl-7-oxabicyclo[4.1.0]heptane, | |
| 3,9-divinyl-2,4,8,10-tetraoxaspiro[5.5]undecene; | 63 |
| 3-butenyl vinyl ether; | |
| di(3-butenyl)ether; | |
| 4-pentenyl ethyl ether; | |
| 5-hexenyl n-propyl ether; | |
| 6-heptenyl isopropyl ether; | |
| 7-octenyl n-butyl ether; | |
| 8-nonenyl isobutyl ether; | |
| 9-decenyl n-pentyl ether; | |
| 10-undecenyl n-hexyl ether; | |
| 3-butenyl cyclohexyl ether; | |
| 4-pentenyl n-octyl ether; | |
| 5-hexenyl isooctyl ether; | |
| 6-heptenyl n-nonyl ether; | |
| 7-octenyl n-decyl ether; | |
| 8-nonenyl n-dodecyl ether; | |
| 9-decenyl hexadecyl ether; | |
| 10-undecenyl benzyl ether; | |
| 3-butenyl 2,2,2-trifluoroethyl ether; | |
| 4-pentenyl phenyl ether; | |
| 5-hexenyl p-chlorophenyl ether; | |
| 6-heptenyl o-tolyl ether; | |
| 7-octenyl p-methoxy ether; | |
| 8-nonenyl 2,6,8-trimethyl-4-nonyl ether; | |
| 9-decenyl N,N-dimethylaminoethyl ether; | |
| 3-butenyl N,N-dimethylaminoethyl ether; | |
| 3-butenyl allyl ether; | |
| 4-pentenyl glycidyl ether; | |
| 5-hexenyl phenyl ether; | |
| 6-heptenyl p-methylphenyl ether; | |
| 7-octenyl p-t-butylphenyl ether; | |
| 8-nonenyl p-methoxyphenyl ether; | |
| 9-decenyl p-chlorophenyl ether; | |
| 10-undecenyl p-bromophenyl ether; | |
| 3-butenyl p-trifluoromethylphenyl ether; | |
| 4-pentenyl p-methoxyphenyl ether; | |
| 5-hexenyl(tetrahydro-1,1-dioxo-3-thienyl) ether. | |

3. Thioethers

| | Compound No. |
|---|---|
| diallyl sulfide; | 36 |
| allyl methyl sulfide; | |
| allyl ethyl sulfide; | |
| allyl n-propyl sulfide; | |
| allyl isopropyl sulfide; | |
| allyl n-butyl sulfide; | |
| allyl isobutyl sulfide; | |
| allyl n-pentyl sulfide; | |
| allyl n-hexyl sulfide; | |
| allyl cyclohexyl sulfide; | |
| allyl n-octyl sulfide; | |
| allyl isooctyl sulfide; | |
| allyl decyl sulfide | |

| | Compound No. |
|---|---|
| allyl hexadecyl sulfide; | |
| allyl benzyl sulfide; | |
| allyl phenyl sulfide; | 35 |
| allyl p-chlorophenyl sulfide; | |
| methyl vinyl sulfide; | |
| ethyl vinyl sulfide; | |
| n-propyl vinyl sulfide; | |
| n-butyl vinyl sulfide; | |
| n-hexyl vinyl sulfide; | |
| cyclohexyl vinyl sulfide; | |
| n-octyl vinyl sulfide; | |
| hexadecyl vinyl sulfide; | |
| allyl vinyl sulfide; | |
| benzyl vinyl sulfide; | |
| phenyl vinyl sulfide; | |
| p-tert-butylphenyl vinyl sulfide; | |
| o-tolyl vinyl sulfide; | |
| p-chlorophenyl vinyl sulfide; | 37 |
| 3-butenyl methyl sulfide; | |
| 4-pentenyl ethyl sulfide; | |
| 5-hexenyl n-propyl sulfide; | |
| 6-heptenyl isopropyl sulfide; | |
| 7-octenyl n-butyl sulfide; | |
| 8-nonenyl isobutyl sulfide; | |
| 9-decenyl n-pentyl sulfide; | |
| 10-undecenyl n-hexyl sulfide; | |
| 3-butenyl cyclohexyl sulfide; | |
| 4-pentenyl n-octyl sulfide; | |
| 5-hexenyl isooctyl sulfide; | |
| 6-heptenyl decyl sulfide; | |
| 7-octenyl hexadecyl sulfide; | |
| 8-nonenyl benzyl sulfide; | |
| 9-decenyl phenyl sulfide; | |
| 10-undecencyl p-chlorophenyl sulfide; | |
| 3-butenyl benzyl sulfide; | |
| 4-pentenyl p-tert-butylphenyl sulfide; | |
| 5-hexenyl o-tolyl sulfide; | |
| 6-heptenyl p-bromophenyl sulfide; | |
| di(3-butenyl) sulfide. | |

4. Esters
| | Compound No. |
|---|---|
| divinyl carbonate; | |
| diallyl carbonate; | 52 |
| dimethallyl carbonate; | |
| allyl N-methyl carbamate; | 54 |
| allyl N-ethyl carbamate; | |
| allyl N-propyl carbamate; | |
| allyl N-n-butyl carbamate; | |
| allyl N-n-octyl carbamate; | |
| allyl N-dodecyl carbamate; | |
| allyl N-phenyl carbamate; | |
| allyl 2-furoate; | 53 |
| methyl acrylate; | |
| ethyl acrylate; | 42, 43 |
| n-propyl acrylate; | |
| isopropyl acrylate; | |
| n-butyl acrylate; | |
| n-pentyl acrylate; | |
| n-hexyl acrylate; | |
| cyclohexyl acrylate; | |
| n-octyl acrylate; | |
| n-decyl acrylate | |
| n-dodecyl acrylate; | 44 |
| n-octadecyl acrylate; | |
| benzyl acrylate; | |
| phenyl acrylate; | |
| p-chlorophenyl acrylate; | |
| 1,2-ethylene diacrylate; | 45 |
| 1,4-tetramethylene diacrylate; | |
| 1,6-hexamethylene diacrylate; | |
| 1,8-octamethylene diacrylate; | |
| 1,10-decamethylene diacrylate; | |
| 1,12-dodecamethylene diacrylate; | |
| methyl methacrylate; | |
| ethyl methacrylate; | |
| propyl methacrylate; | |
| isopropyl methacrylate; | |
| n-butyl methacrylate; | |
| hexyl methacrylate; | |
| cyclohexyl methacrylate; | |
| n-octyl methacrylate; | |
| n-decyl methacrylate; | |
| n-dodecyl methacrylate | |
| 2-hydroxyethyl methacrylate; | |
| benzyl methacrylate; | |
| allyl methacrylate; | |
| phenyl methacrylate; | |
| p-chlorophenyl methacrylate; | |
| tert-butylaminoethyl methacrylate; | |
| N-N-dimethylaminoethyl methacrylate; | |
| 1,2-ethylene dimethacrylate; | |
| 1,4-tetramethylene dimethacrylate; | |
| 1,6-hexamethylene dimethacrylate; | |
| 3-butenyl vinyl carbonate; | |
| 4-pentenyl allyl carbonate | |
| 5-hexenyl methallyl carbonate; | |
| 6-heptenyl N-methyl carbamate; | |
| 7-octenyl N-ethyl carbamate; | |
| 8-nonenyl N-propyl carbamate; | |
| 9-decenyl N-n-butyl carbamate; | |
| 10-undecenyl N-n-octyl carbamate; | |
| 3-butenyl N-dodecylcarbamate; | |
| 4-pentenyl N-phenyl carbamate; | |
| 5-hexenyl 2-furoate; | |
| methyl 6-heptenoate; | |
| ethyl 7-octenoate; | |
| n-propyl 8-nonenoate; | |
| isopropyl 9-decenoate; | |
| n-butyl 10-undecenoate; | |
| n-pentyl 3-butenoate; | |
| n-hexyl 4-pentenoate; | |
| cyclohexyl 5-hexenoate; | |
| n-octyl 6-heptenoate; | |
| n-decyl 7-octenoate; | |
| n-dodecyl 8-nonenoate; | |
| n-octadecyl 9-decenoate; | |
| benzyl 10-undecenoate; | |
| phenyl 3-butenoate; | |
| p-chlorophenyl 4-pentenoate; | |
| 1,2-ethylene di(4-pentenoate); | |
| 1,4-tetramethylene di(5-hexenoate); | |
| 1,6-hexamethylene di(6-heptenoate); | |
| 1,8-octamethylene di(7-octenoate); | |
| 1,10-decamethylene di(8-nonenoate); | |
| 1,12-dodecamethylene di(9-decenoate); | |
| methyl 1-methyl di(10-undecenoate); | |
| ethyl 1-methyl-3-butenoate; | |
| propyl 1-methyl-4-pentenoate; | |
| isopropyl 1-methyl-5-hexenoate; | |
| n-butyl 1-methyl-6-heptenoate; | |
| hexyl 1-methyl-7-octenoate; | |
| cyclohexyl 1-methyl-8-nonenoate; | |
| n-octyl 1-methyl-9-decenoate; | |
| n-decyl 1-methyl-10-undecenoate; | |
| n-dodecyl 1-methyl-3-butenoate; | |
| 2-hydroxyethyl 1-methyl-4-pentenoate; | |
| benzyl 1-methyl-5-hexenoate; | |
| allyl 1-methyl-6-heptenoate; | |
| phenyl 1-methyl-7-octenoate; | |
| p-chlorophenyl 1-methyl-8-nonenoate; | |
| tert-butylaminoethyl 1-methyl-9-decenoate; | |
| N,N-dimethylaminoethyl 1-methyl-10-undecenoate; | |
| 1,2-ethylene di(1-methyl-3-butenoate); | |
| 1,4-tetramethylene di(1-methyl-4-pentenoate); | |
| 1,6-hexamethylene di-(1-methyl-5-hexenoate). | |

5. Amides
| | Compound No. |
|---|---|
| acrylamide; | 38 |
| N-methylacrylamide; | |
| N-hydroxymethylacrylamide; | 40 |
| N-ethylacrylamide; | |
| N-isopropylacrylamide; | |
| N-n-butylacrylamide; | |
| N-tert-butylacrylamide; | 39 |
| N-n-octylacrylamide; | |
| N-dodecylacrylamide; | |

| | Compound No. |
|---|---|
| N,N'-methylenebisacrylamide; | 41 |
| N-phenylacrylamide; | |
| N,N'-tetramethylenebisacrylamide; | |
| N,N'-hexamethylenebisacrylamide; | |
| N-allylacrylamide; | |
| methacrylamide; | |
| N-methylmethacrylamide; | |
| N-ethylmethacrylamide; | |
| N-isopropylmethacrylamide; | |
| N-n-butylmethacrylamide; | |
| N-hexadecylmethacrylamide; | |
| N-tert-butylmethacrylamide; | |
| N-octadecylmethacrylamide; | |
| N-phenylmethacrylamide; | |
| N,N-dimethylmethacrylamide; | |
| N,N-diethylmethacrylamide; | |
| N,N-di-n-butylmethacrylamide; | |
| N,N-di-n-octylmethacrylamide; | |
| N-methyl-3-butenamide; | |
| N-hydroxy-4-pentenamide; | |
| N-ethyl-5-hexenamide; | |
| N-isopropyl-6-heptenamide; | |
| N-n-butyl-7-octenamide; | |
| N-tert-butyl-8-nonenamide; | |
| N-n-octyl-9-decenamide; | |
| N-dodecyl-10-undecenamide; | |
| N-phenyl-3-butenamide; | |
| N,N'-methylenebis(4-pentenamide); | |
| N-phenyl-5-hexenamide; | |
| N,N'-tetramethylenebis(6-heptenamide); | |
| N,N'-hexamethylenebis(7-octenamide); | |
| N-allyl-8-nonenamide; | |
| 1-methyl-9-decenamide; | |
| N-methyl-1-methyl-10-undecenamide; | |
| N-ethyl-1-methyl-3-butenamide; | |
| N-isopropyl-1-methyl-4-pentenamide; | |
| N-n-butyl-1-methyl-5-hexenamide; | |
| N-hexadecyl-1-methyl-6-heptenamide; | |
| N-tert-butyl-1-methyl-7-octenamide; | |
| N-octadecyl-1-methyl-8-nonenamide; | |
| N-phenyl-1-methyl-9-decenamide; | |
| N-phenyl-1-methyl-10-undecenamide; | |
| N-phenyl-1-methyl-3-butenamide; | |
| N,N-dimethyl-1-methyl-4-pentenamide; | |
| N,N-diethyl-1-methyl-5-hexenamide; | |
| N,N-di-n-butyl-1-methyl-6-heptenamide; | |
| N,N-di-n-octyl-1-methyl-7-octenamide. | |

6. Phosphonates

| | |
|---|---|
| diethyl vinylphosphonate; | 51 |
| di-n-butyl-vinylphosphonate; | |
| di-n-hexyl vinylphosphonate; | |
| dicyclohexyl vinylphosphonate; | |
| di-n-octyl vinylphosphonate; | |
| di-dodecyl vinylphosphonate; | |
| di-hexadecyl vinylphosphonate; | |
| dibenzyl vinylphosphonate; | |
| diphenyl vinylphosphonate; | |
| diethyl 1-ethoxyvinylphosphonate. | 64 |

7. Pyridines

| | |
|---|---|
| 2-vinylpyridine; | 55 |
| 3-vinylpyridine; | 57 |
| 4-vinylpyridine; | 56 |
| 2-methyl-5-vinylpyridine; | |
| 5-methyl-2-vinylpyridine; | |
| 6-methyl-2-vinylpyridine; | |
| 6-butyl-2-vinylpyridine; | |
| 2,6-dimethyl-4-vinylpyridine; | |
| 4-t-butyl-2-vinylpyridine; | |
| 2-allylpyridine; | |
| 3-allylpyridine; | |
| 4-allylpyridine; | |
| 2-(3-butenyl)pyridine; | |
| 3-(3-butenyl)pyridine; | |
| 4-(3-butenyl)pyridine; | |
| 3-(4-pentenyl)pyridine; | |
| 4-(5-hexenyl)pyridine; | |
| 2-methyl-5(3-butenyl)pyridine; | |
| 2-methyl-5(7-heptenyl)pyridine; | |
| 2-methyl-5(9-nonenyl)pyridine; | |
| 5-methyl-2(4-pentenyl)pyridine; | |
| 5-methyl-2(6-hexenyl)pyridine; | |
| 5-methyl-2(8-octenyl)pyridine; | |
| 5-methyl-2(10-decenyl)pyridine; | |
| 6-methyl-2-(3-butenyl)pyridine; | |
| 6-butyl-2-(4-pentenyl)pyridine; | |
| 2,6-dimethyl-2-(3-butenyl)pyridine; | |
| 2,6-dimethyl-2-(5-hexenyl)pyridine; | |
| 4-t-butyl-2-(6-heptenyl)pyridine. | |

8. Other Nitrogen Heterocycles

| | |
|---|---|
| N-vinyl imidazole; | 50 |
| N-vinyl-2-methyl imidazole; | |
| N-vinyl-2-phenyl imidazole; | |
| N-vinyl-4,5-dimethyl imidazole; | |
| N-vinyl-4,5-diphenyl imidazole; | |
| N-vinyl carbazole; | 48 |
| N-vinyl-2-pyrrolidinone; | 49 |
| N-(3-butenyl)imidazole; | |
| N-(5-hexenyl)imidazole; | |
| N-(6-heptenyl)-2-methyl imidazole; | |
| N-(7-octenyl)-2-phenyl imidazole; | |
| N-(8-nonenyl)-4,5-dimethyl imidazole; | |
| N-(9-decenyl)-4,5-diphenyl imidazole; | |
| N-(10-undecenyl)carbazole; | |
| N-(3-butenyl)-2-pyrrolidinone; | |
| N-(5-hexenyl)-2-pyrrolidinone; | |
| N-(7-octenyl)-2-pyrrolidinone. | |

9. Ureas

| | |
|---|---|
| allyl urea; | 46 |
| N-allyl-N'-phenyl-urea; | |
| N-allyl-N'-benzoyl urea; | |
| N-allyl-N'-butyl | |
| N-allyl-N'-methyl urea; | |
| N-allyl-N'-n-octyl urea; | |
| N,N'-diallyl urea; | |
| N-allyl-N',N'-dimethyl urea; | |
| N-allyl-N',N'-dibutyl urea; | |
| N-allyl-N',N'-diphenyl urea; | |
| N-(3-butenyl)urea; | |
| N-(4-pentenyl)-N'-phenyl urea; | |
| N-(5-hexenyl)-N'-benzoyl urea; | |
| N-(6-heptenyl)-N'-butyl urea; | |
| N-(7-octenyl)-N'-methyl urea; | |
| N-(8-nonenyl)-N'-n-octyl urea; | |
| N,N'-di(9-decenyl) urea; | |
| N-(10-undecenyl)-N',N'-dimethyl urea; | |
| N-(3-butenyl)-N',N'-dibutyl urea; | |
| N-(4-pentenyl)-N',N'-diphenyl urea. | |

10. Thioureas

| | |
|---|---|
| allyl thiourea; | 47 |
| N-allyl-N'-benzoyl thiourea; | |
| N-allyl-N'-butyl thiourea; | |
| N-allyl-N'-methyl thiourea; | |
| N-allyl-N' -n-octyl thiourea; | |
| N-allyl-N'-phenyl thiourea; | |
| N,N'-diallyl thiourea; | |
| N-allyl-N',N'-dimethyl thiourea; | |
| N-allyl-N',N'-dibutyl thiourea; | |
| N-allyl-N',N'-diphenyl thiourea; | |
| N-(3-butenyl)thiourea; | |
| N-(4-pentenyl)-N'-benzoyl thiourea; | |
| N-(5-hexenyl)-N'-butyl thiourea; | |
| N-(6-heptenyl)-N'-methyl thiourea; | |
| N-(7-octenyl)-N'-n-octyl thiourea; | |
| N-(8-nonenyl)-N'-phenyl thiourea; | |
| N,N'-di(9-decenyl)thiourea; | |
| N-(10-undecenyl)-N',N'-dimethyl thiourea; | |
| N-(3-butenyl)-N',N'-dibutyl thiourea; | |
| N-(4-pentenyl)-N',N'-diphenyl thiourea. | |

11. Silanes vinyltrimethoxysilane;

| | Compound No. |
|---|---|
| vinyltriethoxysilane; | 59 |
| vinyltributoxysilane; | |
| vinyltrihexyloxysilane; | |
| vinyltricyclohexyloxysilane; | |
| vinyltrioctoxysilane; | |
| vinyltriphenoxysilane; | |
| vinyltribenzyloxysilane; | |
| divinyldimethylsilane; | |
| allyltrimethoxysilane; | |
| allyltriethoxysilane; | |
| allyltributoxysilane; | |
| allyltricyclohexyloxysilane; | |
| allyltriphenoxysilane; | |
| (3-butenyl)trimethoxysilane; | |
| (4-pentenyl)triethoxysilane; | |
| (5-hexenyl)tributoxysilane; | |
| (6-heptenyl)trihexyloxysilane; | |
| (7-octenyl)tricyclohexyloxysilane; | |
| (8-nonenyl)trioctoxysilane; | |
| (9-decenyl)triphenoxysilane; | |
| (10-undecenyl)tribenzyloxysilane; | |
| (3-butenyl)tribenzyloxysilane; | |
| (4-pentenyl)triphenoxysilane; | |
| (5-hexenyl)trioctoxysilane; | |
| (6-heptenyl)tricyclohexyloxysilane; | |
| (7-octenyl)trihexyloxysilane. | |
| 12. Alcohols | |
| allyl alcohol; | 62 |
| methallyl alcohol; | |
| 3-buten-1-ol; | |
| 2-methyl-2-propen-1-ol; | |
| 4-penten-1-ol; | |
| 4-penten-2-ol; | |
| 1-penten-3-ol; | |
| 2-methyl-3-buten-1-ol; | |
| 3-methyl-3-buten-1-ol; | |
| 2-methyl-4-penten-2-ol; | |
| 4-methyl-1-penten-3-ol; | |
| 1,5-hexadien-3-ol; | |
| 9-decen-1-ol; | |
| 10-undecen-1-ol; | |
| 1-(tetrahydro-1,1-dioxo-2-thienyl)-3-buten-2-ol; | 58 |
| 5-hexen-1-ol; | |
| 6-hepten-1-ol; | |
| 7-octen-1-ol; | |
| 8-nonen-1-ol. | |
| 13. Nitriles | |
| acrylonitrile; | 61 |
| methacrylonitrile; | |
| allyl cyanide; | |
| 3-butenenitrile; | |
| 4-pentenenitrile; | |
| 5-hexenenitrile; | |
| 6-heptenenitrile; | |
| 7-octenenitrile; | |
| 8-nonenenitrile; | |
| 9-decenenitrile; | |
| 10-undecenenitrile. | |
| 14. Benzenes | |
| o-vinylbenzene; | |
| m-vinylbenzene; | |
| p-divinylbenzene; | |
| m-diisopropenylbenzene; | 60 |
| p-diisopropenylbenzene; | |
| allyl (3,4-methylenedioxy)benzene; | |
| 2-chlorostyrene; | |
| 3-chlorostyrene; | |
| 4-chlorostyrene; | |
| 4-methylstyrene; | |
| o-methylstyrene; | |
| 4-methoxystyrene; | |
| 4-ethoxystyrene; | |
| 2,5-dimethoxystyrene | |
| 2,5-dichlorostyrene; | |
| (3-butenyl)benzene; | |
| (4-pentenyl)benzene; | |
| p-di(5-hexenyl)benzene; | |
| m-di(6-heptenyl)benzene; | |
| p-di(6-heptenyl)benzene; | |
| 7-octenyl-(3,4-methylenedioxy)benzene; | |
| 2-chloro-(7-octenyl)benzene; | |
| 3-bromo-(8-nonenyl)benzene; | |
| 4-chloro-(9-decenyl)benzene; | |
| 4-methyl-(10-undecenyl)benzene; | |
| 2-methyl-(3-butenyl)benzene; | |
| 4-methoxy-(4-pentenyl)benzene; | |
| 4-ethoxy-(5-hexenyl)benzene; | |
| 2,5-dimethoxy-(6-heptenyl)benzene; | |
| 2,5-dichloro-(7-octenyl)benzene; | |
| 2-trifluoromethyl-(8-nonenyl)benzene; | |
| 2,5-dibromo-)benzene. | |

Trimethyl tin hydride having the following formula is used in this invention: $(CH_3)_3Sn\text{-}H$. This organotin hydride is prepared by known procedures such as are described in the following references:

K. Hayashi, J. Iyoda and I. Shiihara, *J. Organometal. Chem.*, 10, 81 (1967).

H. G. Kuivila, *Advan. Organometal Chem.*, 1, 47 (1964).

W. P. Neumann, *Agnew. Chem., Internat. Edit.*, 2, 165 (1963).

Application of the compounds of the invention as insecticides and herbicides can be carried out in a number of ways. For practical applications, the compounds of the invention can be used alone, or dissolved or suspended in suitable carriers such as water, alcohols, ketones, phenols, toluene or xylenes. Optionally, one or more surface active agents and/or inert diluents can be added to the formulation to facilitate handling. The formulations can take the form of dusts, granules, wettable powders, pastes, emulsifiable concentrates, aerosols, water solution concentrates, or a water soluble solid.

For example, the compounds of the invention can be applied as dusts when admixed with or absorbed on powdered solid carriers, such as the various mineral silicates, e.g., mica, talc, pyrophillite and clays, or as liquids or sprays when in a liquid carrier, as in solution in a suitable solvent such as acetone, benzene or kerosene, or dispersed in a suitable non-solvent medium, for example, water. In protecting plants (the term including plant parts), the chemicals of the present invention are preferably applied as aqueous emulsions containing a surface-active dispersing agent which may be an anionic, nonionic or cationic surface-active agent. Such surface-active agents are well known and reference is made to U.S. Pat. No. 2,547,724, columns 3 and 4, for detailed examples of the same. The chemicals of the invention may be mixed with such surface-active dispersing agents, with or without an organic solvent, as concentrates for subsequent addition of water to make aqueous suspensions of the chemicals of the desired concentration. The chemicals of the invention may be admixed with powdered solid carriers, such as mineral silicates together with a surface-active dispersing agent so that a wettable powder is obtained which may then be applied directly to loci to be protected, or may be shaken with water to form a suspension of the chemical (and powdered) solid carrier) in water for application in that form. The chemicals of the present invention may be applied to loci to be protected by the aerosol method.

Solutions for aerosol treatment may be prepared by dissolving the chemical directly in the aerosol carrier which is liquid under pressure but which is a gas at ordinary temperature (e.g., 20° C.) and atmospheric pressure, or the aerosol solution may be prepared by first dissolving the chemical in less volatile solvent and then admixing such solution with the highly volatile liquid aerosol carrier. The chemicals may be used admixed with carriers that are active themselves, for example, other insecticides, acaricides, fungicides or bactericides.

These formulations will contain amounts of the compounds effective for the particular method of control. These amounts can vary widely; typically, the range is from 0.1 to 95% active ingredient. Spray dilutions can contain from a few parts per million to full strength concentrates applied by ultra low volume techniques. Concentration per unit area, where plants are the area treated, can vary from 0.01 to 10 pounds per acre.

Commonly, the compounds are applied directly. To control aphids, for example, sprays of the compounds are applied to the aphids directly, to plants upon which they feed, or both. Sprays applied to the aphid-infested plants kill effectively even if direct contact does not occur, as where the aphids cling to the inner surface of a curled up leaf or lie in a protected leaf sheath of, for example, a grain plant. Another effective method of attack involves application of the compounds to the soil or other medium in which insect-infested plants live. The compounds act systemically upon the insects after the compound is absorbed by the plants.

Harmful insects and related pests, such as mites, attack a wide variety of plants, including both ornamental and agricultural plants such as chrysanthemum, azalea, cotton, corn, wheat, apple and tobacco, and inflict damage by withdrawing vital juices from the plants, by secreting toxins and often by transmitting diseases. The compounds of the invention can prevent such damage. The methods of application, and the selection and concentration of these compounds will, of course, vary depending upon such circumstances as area, climate, prevalent diseases, etc. One skilled in the art can select the proper approach by simple experiments.

The following examples demonstrate the use of the above described procedures in obtaining the organotin compounds of this invention and their utilization as insecticides and herbicides:

. EXAMPLE 1

An 80-ml, two-necked, pyrex glass Schlenk reaction tube fitted with a magnetic stirrer was swept thoroughly with nitrogen and maintained in an air-free condition. The tube was then charged with a mixture of 16.5 g (100 mmoles) of trimethyltin hydride and 5.9 g (50 mmoles) of divinyl sulfone, stoppered and then irradiated by means of a 100 watt mercury vapor lamp for 4 hours. The reaction mixture was maintained at 20° C. and stirred magnetically. Recrystallization of the solid product from petroleum ether gave 15 g of 2,2′-sulfonylbisethyltrimethylstannane, m.p. 78.5°–80.5° C., compound 1 of Table I. The presence of both the sulfonyl and trimethyltin groups was indicated by the strong infrared absorption bands at 1300 cm$^{-1}$, 1240 cm$^{-1}$, 1140 cm$^{-1}$, 1105 cm$^{-1}$ and 765 cm$^{-1}$ using a KBr disc. Nuclear magnetic resonance spectroscopy (NMR) showed the following: the protons alpha to the sulfonyl moiety appeared as a complex multiplet centered at 302 Hz (4 protons), the protons beta to the sulfonyl moiety appeared as a complex multiplet centered at 114.5 Hz (4 protons), the protons of the trimethyltin group appeared at 14.5 Hz, singlet accompanied by one satellite band on either side (9 protons).

Analysis: Calc'd for $C_{10}H_{26}O_2SSn$ (percent): C, 26.9; H, 5.87; S, 7.17; Sn, 53.0. Found: C, 26.9; H, 6.16; S, 6.89; Sn, 52.6.

EXAMPLE 2

This example illustrates the use of a solvent in the reaction described in Example 1.

Using the apparatus and method of Example 1, trimethyltin hydride (46 g, 279 mmoles), divinyl sulfone (16.5 g, 139 mmoles), and 30 ml of benzene were charged into the glass Schlenk reaction tube. The tube was irradiated with stirring at 20° C. under a blanket of nitrogen for 18 hours. After filtration and evaporation of the solvent, the crude product was recrystallized from petroleum ether to give 48.5 g, m.p. 78.3°–79.3°, of 2,2′-sulfonylbisethyltrimethylstannane, compound 2 of Table I. Analysis was the same as in Example 1 above.

Compounds 16, 46 and 53, which are shown in Table I hereinbelow, were respectively prepared using the apparatus of Example 1 and the following specific procedures:

EXAMPLE 3

A mixture of 4.4 ml (5 g, 42.4 mmoles) of divinyl sulfone, 5 ml (42.4 mmoles) of trimethyltin hydride and 5 ml of toluene was irradiated for 18 hours. A liquid residue was obtained after filtration and evaporation of solvent. Five milliliters of piperidine was added to the crude product with stirring and cooling. After stirring for two hours at room temperature, the excess piperidine was removed under reduced pressure leaving 9.2 g of an oil. To a solution of 5.2 g of this oil in 50 ml of benzene was added 1.25 ml of methyl iodide. After stirring for 3 days at room temperature, 2.3 g of a solid was collected by filtration. Purification of the solid by precipitation from an acetone solution with ethyl ether gave 2-(2-piperidinoethylsulfonyl)-ethyltrimethylstannane, methiodide, m.p. 122°–124° C., compound 16 of Table I. The presence of both the sulfonyl and trimethyltin moieties was indicated by the infrared absorption bands at 1305 cm$^{-1}$, 1260 cm$^{-1}$ and 1120 cm$^{-1}$ and at 770 cm$^{-1}$, using a KBr disc.

Analysis: Calc'd for $C_{13}H_{30}INO_2SSn$ (percent): C, 30.61; H, 5.93; N, 2.75. Found: C, 30.08; H, 5.87; N, 2.83.

EXAMPLE 4

A mixture of 8 g (30 mmoles) of 2-(ethoxycarbonyl)-ethyltrimethylstannane (compound 47), 5 ml of 95% hydrazine (150 mmoles) in 10 ml of ethanol was refuxed for 2 hours. The volatiles were removed at reduced pressure. Distillation of the crude product afforded 5.26 g of 2-(hydrazinocarbonyl)ethyltrimethylstannane, b.p. 92°–98°. C. (0.07 mm), compound 42 of Table I. The infrared spectrum of the distillate showed the following characteristic absorptions: 3300 cm$^{-1}$ (N-H), 1660 cm$^{-1}$ and 1530 cm$^{-1}$

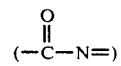

and 760 cm$^{-1}$ (—Sn(CH$_3$)$_3$). A gas chromatogram of the sample showed a single peak on a 6′×⅛″ commercially obtained column packed with 10% on silicone gum rubber on silanized diatomaceous earth. The NMR spectrum exhibited the following proton absorptions: a broad singlet at 752 Hz (1 proton) assigned to N-H, a singlet at 388 Hz (2 protons) assigned to NH$_2$, a triplet centered at 235 Hz (2 protons) assigned to

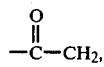

a triplet centered at 98 Hz (2 protons) assigned to CH$_2$-Sn, and a singlet centered at 6 Hz (9 protons) assigned to Sn(CH$_3$)$_3$.

Analysis: Calc'd for C$_6$H$_{16}$N$_2$OSn (percent): C, 28.72; H, 6.43; N, 11.17. Found: C, 28.08; H, 6.44; N, 10.53.

EXAMPLE 5

An 80 ml, two-necked, pyrex glass Schlenk reaction tube containing a Teflon coated magnetic stir bar was swept thoroughly with nitrogen and maintained in an air-free condition. The tube was charged with 10.7 g (42.5 mmoles) of 3-butenyl-4-t-butylphenyl sulfone and 7.0 g (42.5 mmoles) of trimethyltin hydride, stoppered, and placed in a 20° C. water bath. The tube was irradiated for 70 hours by a 100 watt mercury vapor lamp which was situated in a large test tube and placed in the same bath 5-10 cm. from the reaction tube. Recrystallization of the solid product from petroleum ether afforded 3.6 g of 4-(4-t-butylphenylsulfonyl)butyltrimethylstannane, m.p. 80°-81.8° C. The presence of both the sulfonyl and trimethyltin moieties was indicated by strong infrared absorption bands at 1300 cm$^{-1}$, 1282 cm$^{-1}$, 1147 cm$^{-1}$ (—SO$_2$—) and 780 cm$^{-1}$ [(CH$_3$)$_3$Sn—] employing a KBR disc. Nuclear magnetic resonance spectroscopy (NMR) showed the following:

The aromatic protons appeared as two multiplets each centered at 777 and 753 Hz (each having 2 protons); the protons alpha to the sulfonyl moiety appeared as a complex multiplet centered at 307 Hz (2 protons); the methylene protons beta and gamma to the sulfone group appeared as a complex multiplet centered at 162 Hz (4 protons); the methyl protons of the t-butyl group appeared as a singlet at 134 Hz (9 protons); the methylene protons adjacent to the tin atom appeared as a complex moiety centered at 73 Hz (2 protons); the protons of the trimethyltin group appeared at the same chemical shift as tetramethylsilane (the internal standard) ~1 Hz.

Analysis: Calc'd for C$_{17}$H$_{30}$O$_2$SSn (percent): C, 48.94; H, 7.25; S, 7.68; Sn, 28.45. Found: C, 49.06; H, 7.33; S, 8.19; Sn, 27.60.

EXAMPLE 6

The procedure described in Example 5 was employed except that 10.1 g (42.5 mmoles) of 5-hexenyl p-tolyl sulfone and 14.0 g (85 mmoles) of trimethyltin hydride were the reactants. The reaction mixture was irradiated for 232 hours. The excess trimethyltin hydride was allowed to evaporate from the reaction mixture under a flow of nitrogen. The unreacted 5-hexenyl p-tolyl sulfone was removed from the reaction mixture by distillation at 1×10$^{-3}$ mm Hg leaving 3.25 g of crude product. Column chromatography of the distillation residue over silica gel, employing toluene and 1% acetone in toluene as eluents, afforded an oil, 6-(p-tolylsulfonyl)hexyltrimethylstannane. The presence of both the sulfonyl and trimethyltin moieties was indicated by the strong infrared absorption bands at 1315 cm$^{-1}$, 1300 cm$^{-1}$, 1285 cm$^{-1}$ and 1140 cm$^{-1}$ (—SO$_2$—) and 760 cm$^{-1}$ [(CH$_3$)$_3$Sn—]. NMR showed the following:

The aromatic protons appeared as two multiplets each centered at 775 and 732 Hz (2 protons each); the protons alpha to the sulfonyl group appeared as a complex multiplet at 303 Hz (2 protons); the methyl protons of the tolyl group appeared as a singlet at 243 Hz (3 protons); the methylene protons beta through epsilon to the sulfone group appeared as a broadened complex multiplet centered at 147 Hz (8 protons); the protons of the methylene group attached to the tin atom appeared as a triplet centered at 74 Hz (2 protons); the protons of the trimethyltin group appeared as a singlet at −2 Hz accompanied by one satellite band on either side (9 protons).

Analysis: Calc'd for C$_{16}$H$_{28}$O$_2$SSn (percent): C, 47.67; H, 7.00. Found: C, 47.52; H, 7.07.

EXAMPLE 7

The procedure described in Example 5 was employed except that 13.1 g (42.5 mmoles) of 10-undecenyl-p-tolyl sulfone and 14.0 g (85 mmoles) of trimethyltin hydride were the reactants. The reaction mixture was irradiated for 189 hours. The excess trimethyltin hydride was allowed to evaporate from the reaction mixture under a flow of nitrogen. The residual oil weighed 15.5 g. One-half of the crude product was chromatographed on a column containing silica gel using toluene and 2% acetone in toluene as eluents. The product, 11-(p-tolylsulfonyl)undecyltrimethylstannane, was obtained as an oil. The presence of both the sulfonyl and trimethyltin groups was indicated by the strong infrared absorption bands at 1315 cm$^{-1}$, 1300 cm$^{-1}$, 1285 cm$^{-1}$, 1140 cm$^{-1}$ (—SO$_2$—) and 760 cm$^{-1}$ [(CH$_3$)$_3$Sn—]. NMR showed the following:

The aromatic protons appeared as two multiplets each centered at 771 and 728 Hz (2 protons each); the protons alpha to the sulfonyl moiety consisted of a multiplet centered at 300 Hz (2 protons); the methyl protons of the tolyl group appeared as a singlet at 240 Hz (3 protons); the methylene [—(CH$_2$)$_9$—] appeared as a broadened multiplet with peak maxima at 161 and 119 Hz (18 protons); the methylene protons alpha to the tin atom appeared as a triplet centered at 76 Hz (2 protons); the protons of the trimethyltin group appeared as a singlet at 0 Hz accompanied by one satellite band on either side (9 protons).

Analysis: Calc'd for C$_{21}$H$_{38}$O$_2$SSn (percent): C, 53.29; H, 8.09. Found: C, 53.81; H, 8.09.

EXAMPLE 8

Using the procedures and apparatus described above and detailed in Examples 1 and 2, additional organotin compounds of this invention were prepared and, along with the products of Examples 1-7, are identified in Table I below wherein the expression "high vacuum" denotes a pressure of at least 0.1 mm Hg. Table I also indicates those instances where a solvent was used and/or the compound was purified as well as the melting point or boiling point at a given pressure in millimeters of mercury. All of the compounds are identified as stannanes since they can be regarded as substitution products of "stannane", i.e., SnH$_4$.

The compounds identified by numbers 1-17, 21-23, 25-34, 36, 39-42, 44-47, 49-56, 58-60 and 63-92 are deemed to be novel and to be unobvious over the prior art. The other compounds are either anticipated in the prior art or deemed to be so nearly like prior art compounds as to be obvious variants thereof. The prior art referred to in the two preceding sentences consists of:

J. Appl. Chem. 9, 106–113 (1959);
C. A. 68, 1190 h (1968);
Ayrey et al., supra;
Ziegler British No. 966,813;
Bublitz U.S. Pat. No. 3,591,614;
Bublitz U.S. Pat. No. 3,641,037;
German No. 1,158,974;
J. Appl. Chem. 9, 176 (1959);
J. Appl. Chem. 7, 356 (1957);
Diss. Abstr. 22, 73 (1961);

as well as the art referred to herein under Background of the Invention.

TABLE I

Organotin Compounds of the Formula $(CH_3)_3Sn(CH_2)_n-\underset{\underset{R'}{|}}{C}H-X$

| No. | Stannane Compound | R' | n | X | Reaction Solvent | Purification Method | m.p. or b.p. °C. (mm Hg) |
|---|---|---|---|---|---|---|---|
| 1 | 2,2'-sulfonylbisethyltrimethyl- | H | 1 | $-SO_2CH_2CH_2Sn(CH_3)_3$ | none | recryst'n | 78.5–80.5 |
| 2 | 2,2'-sulfonylbisethyltrimethyl- | H | 1 | $-SO_2CH_2CH_2Sn(CH_3)_3$ | benzene | recryst'n | 78.3–79.3 |
| 3 | trimethyl-2-(methylsulfonyl)ethyl- | H | 1 | $-SO_2CH_3$ | none | recryst'n | 51–53 |
| 4 | 2-(ethylsulfonyl)ethyltrimethyl- | H | 1 | $-SO_2C_2H_5$ | toluene | distillation | 98–108 (0.1–.2) |
| 5 | trimethyl-2-(i-propylsulfonyl)ethyl- | H | 1 | $-SO_2-i-C_3H_7$ | none | distillation | 90–98 (0.01) |
| 6 | 2-(s-butylsulfonyl)ethyltrimethyl- | H | 1 | $-SO_2CH(CH_3)CH_2CH_3$ | none | distillation | 96–99 (0.06) |
| 7 | trimethyl-2-(t-pentylsulfonyl)ethyl- | H | 1 | $-SO_2C(CH_3)_2CH_2CH_3$ | none | distillation | 97–102 (0.07–0.09) |
| 8 | trimethyl-2-(n-octylsulfonyl)ethyl- | H | 1 | $-SO_2-n-C_8H_{17}$ | none | high vacuum | oil |
| 9 | 2-(n-dodecylsulfonyl)ethyltrimethyl- | H | 1 | $-SO_2-n-C_{12}H_{25}$ | toluene | high vacuum | oil |
| 10 | trimethyl-2-(n-octadecylsulfonyl)ethyl- | H | 1 | $-SO_2-n-C_{18}H_{37}$ | toluene | recryst'n | 55–55.5 |
| 11 | 2-(cyclohexylsulfonyl)ethyltrimethyl- | H | 1 |  | none | destillation | 140–50 (.07–.15) |
| 12 | 2-(benzylsulfonyl)ethyltrimethyl- | H | 1 |  | acetonitrile | high vacuum | oil |
| 13 | trimethyl-2-(phenylsulfonyl)ethyl- | H | 1 |  | none | high vacuum | oil |
| 14 | 2-(p-t-butylphenylsulfonyl)ethyltrimethyl- | H | 1 |  | toluene | recryst'n | 118–20 |
| 15 | 2-(p-chlorophenylsulfonyl)ethyltrimethyl- | H | 1 |  | none | recryst'n | 57–60 |
| 16 | 2-(2-piperidinoethylsulfonyl)ethyltrimethyl, methiodide | H | 1 |  | none | ether wash | 122–24 |
| 17 | 2,2'-(ethylenedisulfonyl)-bisethyltrimethyl- | H | 1 | $-SO_2(CH_2)_2SO_2(CH_2)_2Sn(CH_3)_3$ | ethyl acetate | recryst'n | 141.5 (decomp.) |
| 18 | 2-ethoxyethyltrimethyl- | H | 1 | $-OC_2H_5$ | none | distillation | 80–82 (50) |
| 19 | 2-n-butoxyethyltrimethyl- | H | 1 | $-O-n-C_4H_9$ | none | distillation | 86–91 (15) |
| 20 | 2-i-butoxyethyltrimethyl- | H | 1 | $-OCH_2CH(CH_3)_2$ | none | distillation | 95–98 (30) |
| 21 | trimethyl-2-i-octoxyethyl- | H | 1 | $-O-i-C_8H_{17}$ | none | distillation | 58–62 (0.05) |
| 22 | 2-decoxyethyltrimethyl- | H | 1 | $-OC_{10}H_{21}$ | none | distillation | 68–71 (0.03) |
| 23 | 2-dodecoxyethyltrimethyl- | H | 1 | $-OC_{12}H_{25}$ | none | distillation | 113–17 (.07) |
| 24 | 3-(2,3-epoxypropoxy)-propyltrimethyl- | H | 2 | $-OCH_2\overset{O}{\overset{/\backslash}{C}H}CH_2$ | none | distillation | 100–2 (4.5) |
| 25 | 2,2'-oxybisethyltrimethyl- | H | 1 | $-OCH_2CH_2Sn(CH_3)_3$ | none | distillation | 55–58 (0.1) |
| 26 | 3,3'-oxybispropyltrimethyl- | H | 2 | $-OCH_2CH_2CH_2Sn(CH_3)_3$ | none | distillation | 74–5 (0.07) |
| 27 | trimethyl-3-phenoxypropyl- | H | 2 |  | none | distillation | 66–70 (0.025) |
| 28 | 3-(p-t-butylphenoxy)propyltrimethyl- | H | 2 |  | none | distillation | 98–100 (0.08) |

TABLE I-continued

Organotin Compounds of the Formula $(CH_3)_3Sn(CH_2)_n-\underset{\underset{X}{|}}{\overset{\overset{R'}{|}}{C}}H$

| No. | Stannane Compound | R' | n | X | Reaction Solvent | Purification Method | m.p. or b.p. °C. (mm Hg) |
|---|---|---|---|---|---|---|---|
| 29 | trimethyl-3-(p-methoxyphenoxy)propyl- | H | 2 | $-O-\text{C}_6\text{H}_4-OCH_3$ | none | distillation | 98–100 (0.1) |
| 30 | 3-(p-chlorophenoxy)propyltrimethyl- | H | 2 | $-O-\text{C}_6\text{H}_4-Cl$ | none | distillation | 84–88 (0.07) |
| 31 | 2-(2,2,2-trifluoroethoxy)ethyltrimethyl | H | 1 | $-OCH_2CF_3$ | none | distillation | 81–86 (50) |
| 32 | 2-(N,N-dimethylaminoethoxy)ethyltrimethyl- | H | 1 | $-OCH_2CH_2N(CH_3)_2$ | none | distillation | 43–43.5 (0.07–0.03) |
| 33 | 2-(hexadecoxy)ethyltrimethyl- | H | 1 | $-OC_{16}H_{33}$ | none | high vacuum | oil |
| 34 | 3-(tetrahydro-1,1-dioxo 3-thienyloxy)propyltrimethyl- | H | 2 | $-O-$(tetrahydrothiophene-1,1-dioxide-3-yl) | none | high vacuum | oil |
| 35 | trimethyl-3-phenylthiopropyl- | H | 2 | $-S-\text{C}_6\text{H}_5$ | none | distillation | 82.5–7 (0.06) |
| 36 | 3,3'-thiobispropyltrimethyl- | H | 2 | $-SCH_2CH_2CH_2Sn(CH_3)_3$ | none | distillation | 94–98 (0.06) |
| 37 | 2-(p-chlorophenylthio)ethyltrimethyl- | H | 1 | $-S-\text{C}_6\text{H}_4-Cl$ | none | distillation | 90–92 (0.07) |
| 38 | 2-carbamoylethyltrimethyl- | H | 1 | $-\overset{O}{\overset{\|}{C}}-NH_2$ | tetrahydrofuran | recryst'n | 69–70.2 |
| 39 | 2-(N-t-butylcarbamoyl)ethyltrimethyl- | H | 1 | $-\overset{O}{\overset{\|}{C}}-NHC(CH_3)_3$ | tetrahydrofuran | recryst'n | 74–75.5 |
| 40 | 2-(N-hydroxymethylcarbamoyl)ethyltrimethyl- | H | 1 | $-\overset{O}{\overset{\|}{C}}-NHCH_2OH$ | tetrahydrofuran | recryst'n | 79–84 |
| 41 | N,N'-methylenebis(2-carbamoylethyltrimethyl-) | H | 1 | $-\overset{O}{\overset{\|}{C}}-\overset{H}{\overset{\|}{N}}CH_2\overset{HO}{\overset{\|}{N}}\overset{\|}{C}(CH_2)_2Sn(CH_3)_3$ | acetonitrile | recryst'n | 128–8.5 |
| 42 | 2-(hydrazinocarbonyl)ethyltrimethyl- | H | 1 | $-\overset{O}{\overset{\|}{C}}-NHNH_2$ | ethanol | distillation | 92–98 (0.07) |
| 43 | 2-(ethoxycarbonyl)ethyltrimethyl- | H | 1 | $-COOC_2H_5$ | none | distillation | 85–6 (10) |
| 44 | 2-(dodecoxycarbonyl)ethyltrimethyl- | H | 1 | $-COO-n-C_{12}H_{25}$ | none | distillation | 116–17 (0.003) |
| 45 | 2,2'-(ethylenedioxydicarbonyl)bisethyltrimethyl- | H | 1 | $-COO(CH_2)_2OOC(CH_2)_2Sn(CH_3)_3$ | none | distillation | 122–30 (0.07–0.1) |
| 46 | trimethyl-3-ureidopropyl- | H | 2 | $-NHCONH_2$ | tetrahydrofuran | recryst'n | 79.5–82 |
| 47 | trimethyl-3-thioureidopropyl- | H | 2 | $-NHCSNH_2$ | tetrahydrofuran | recryst'n | 124.5–125.5 |
| 48 | 2-(N-carbazolyl)ethyltrimethyl- | H | 1 | -(N-carbazolyl) | toluene | recryst'n | 93.5–95.5 |
| 49 | trimethyl-2-(2-oxopyrrolidinyl)ethyl- | H | 1 | -(2-oxopyrrolidin-1-yl) | none | distillation | 69–80 (0.03) |
| 50 | 2-(N-imidazolyl)ethyltrimethyl- | H | 1 | -(N-imidazolyl) | none | distillation | 85–6 (0.1) |
| 51 | 2-(O,O-diethylphosphono)ethyltrimethyl- | H | 1 | $-PO(OC_2H_5)_2$ | none | distillation | 49.5–51 (0.02) |
| 52 | 3,3'-(carbonyldioxy)bispropyltrimethyl- | H | 2 | $-OCOO(CH_2)_3Sn(CH_3)_3$ | none | distillation | 104–108 (0.05) |
| 53 | 3-(2-furoyloxy)propyltrimethyl- | H | 2 | $-OCO-\text{(2-furyl)}$ | none | distillation | 92–95 (0.1) |
| 54 | 3-(N-methylcarbamoyloxy)propyltrimethyl- | H | 2 | $-OCONHCH_3$ | none | distillation | 78–81 (0.15) |

TABLE I-continued

Organotin Compounds of the Formula $(CH_3)_3Sn(CH_2)_n-\overset{R'}{\underset{|}{C}H}-X$

| No. | Stannane Compound | R' | n | X | Reaction Solvent | Purification Method | m.p. or b.p. °C. (mm Hg) |
|---|---|---|---|---|---|---|---|
| 55 | 2-(2-pyridyl)ethyltrimethyl- | H | 1 | 2-pyridyl | none | distillation | 56 (0.1) |
| 56 | 2-(2-methyl-5-pyridyl)ethyltrimethyl- | H | 1 | 2-methyl-5-pyridyl | none | distillation | 72-7 (0.05) |
| 57 | 2-(4-pyridyl)ethyltrimethyl- | H | 1 | 4-pyridyl | none | distillation | 63-66 (0.15) |
| 58 | 4-(tetrahydro-1,1-dioxo-2-thienyl)-3-hydroxybutyltrimethyl- | OH | 2 | —CH$_2$-(tetrahydro-2-thienyl-1,1-dioxide) | none | recrystall'n | 99-103.5 |
| 59 | 2-(triethoxysilyl)ethyltrimethyl- | H | 1 | —Si(OC$_2$H$_5$)$_3$ | none | distillation | 56-7 (0.09) |
| 60 | 2,2'-m-phenylenebispropyltrimethyl- | CH$_3$ | 1 | m-C$_6$H$_4$-CH(CH$_3$)CH$_2$Sn(CH$_3$)$_3$ | none | distillation | 110-11 (0.1) |
| 61 | 2-cyanoethyltrimethyl- | H | 1 | —CN | none | distillation | 87-9 (10) |
| 62 | 3-(hydroxypropyl)trimethyl- | H | 2 | —OH | none | distillation | 37-8 (0.1) |
| 63 | 2,2'-[2,4,8,10-tetraoxaspiro[5.5]undec-3,9-ylene]-bisethyltrimethyl- | H | 1 | —CH(O-)$_2$ spiro C(CH(CH$_2$)$_2$Sn(CH$_3$)$_3$)(O-)$_2$ | none | distillation | 144 (0.0025) |
| 64 | 2-ethoxy-2(O,O-diethylphosphono)ethyltrimethyl- | OC$_2$H$_5$ | 1 | —PO(OC$_2$H$_5$)$_2$ | none | distillation | 79 (0.45-0.05) |
| 65 | 2-(2,6,8-trimethyl-4-nonoxy)ethyltrimethyl- | H | 1 | —OC(H)(CH$_2$CH(CH$_3$)$_2$)(CH$_2$CH(CH$_3$)CH$_2$CH(CH$_3$)$_2$) | none | distillation | 67-71 (0.003) |
| 66 | 2-(p-tolylsulfonyl)ethyltrimethyl- | H | 1 | —SO$_2$—C$_6$H$_4$—CH$_3$ | tetrahydrofuran | recrystall'n | 55.5-58 |
| 67 | 2-(p-ethylphenylsulfonyl)ethyltrimethyl- | H | 1 | —SO$_2$—C$_6$H$_4$—CH$_2$CH$_3$ | tetrahydrofuran | recrystall'n | 52-56.5 |
| 68 | 2-(p-isopropylphenylsulfonyl)ethyltrimethyl- | H | 1 | —SO$_2$—C$_6$H$_4$—CH(CH$_3$)$_2$ | tetrahydrofuran | recrystall'n | 53-57.5 |
| 69 | 2-(p-n-pentylphenylsulfonyl)ethyltrimethyl- | H | 1 | —SO$_2$—C$_6$H$_4$—(CH$_2$)$_4$CH$_3$ | toluene | high vacuum | oil |
| 70 | 2-[p-(1,1-dimethylpropyl)phenylsulfonyl]ethyltrimethyl- | H | 1 | —SO$_2$—C$_6$H$_4$—C(CH$_3$)$_2$CH$_2$CH$_3$ | toluene | recrystall'n | 72-74 |
| 71 | 2-(p-octylphenylsulfonyl)ethyltrimethyl- | H | 1 | —SO$_2$—C$_6$H$_4$—(CH$_2$)$_7$CH$_3$ | tetrahydrofuran | high vacuum | oil |
| 72 | 2-(p-dodecylphenylsulfonyl)ethyltrimethyl- | H | 1 | —SO$_2$—C$_6$H$_4$—C$_{12}$H$_{25}$ | tetrahydrofuran | high vacuum | oil |
| 73 | 2-(p-n-dodecylphenylsulfonyl)ethyltrimethyl- | H | 1 | —SO$_2$—C$_6$H$_4$—(CH$_2$)$_{11}$CH$_3$ | toluene | recrystall'n | 33-34 |
| 74 | 2-(p-n-tridecylphenylsulfonyl)ethyltrimethyl- | H | 1 | —SO$_2$—C$_6$H$_4$—(CH$_2$)$_{12}$CH$_3$ | toluene | recrystall'n | 43.3-44.8 |

TABLE I-continued

Organotin Compounds of the Formula $(CH_3)_3Sn(CH_2)_n-\overset{R'}{\underset{|}{CH}}-X$

| No. | Stannane Compound | R' | n | X | Reaction Solvent | Purification Method | m.p. or b.p. °C. (mm Hg) |
|---|---|---|---|---|---|---|---|
| 75 | 2-(2,4-dimethylphenylsulfonyl)ethyltrimethyl- | H | 1 | $-SO_2-\langle\bigcirc\rangle-CH_3$ with CH_3 | tetrahydrofuran | high vacuum | oil |
| 76 | 2-(2,5-dimethylphenylsulfonyl)ethyltrimethyl- | H | 1 | $-SO_2-\langle\bigcirc\rangle$ with CH_3 (top) and CH_3 (bottom) | tetrahydrofuran | high vacuum | oil |
| 77 | 2-(2,4-diethylphenylsulfonyl)ethyltrimethyl- | H | 1 | $-SO_2-\langle\bigcirc\rangle-CH_2CH_3$ with CH_2CH_3 | tetrahydrofuran | high vacuum | oil |
| 78 | 2-(2,5-diisopropylphenylsulfonyl)ethyltrimethyl- | H | 1 | $-SO_2-\langle\bigcirc\rangle$ with $CH(CH_3)_2$ substituents | tetrahydrofuran | high vacuum | oil |
| 79 | 2-(p-cyclopentylphenylsulfonyl)ethyltrimethyl- | H | 1 | $-SO_2-\langle\bigcirc\rangle-\text{cyclopentyl}$ | tetrahydrofuran | recrystall'n | 94-95 |
| 80 | 2-(p-cyclohexylphenylsulfonyl)ethyltrimethyl- | H | 1 | $-SO_2-\langle\bigcirc\rangle-\text{cyclohexyl}$ | tetrahydrofuran | recrystall'n | 116-118 |
| 81 | 2-(p-bicyclo[2.2.1]hept-2-ylphenylsulfonyl)ethyltrimethyl- | H | 1 | $-SO_2-\langle\bigcirc\rangle-\text{bicycloheptyl}$ | tetrahydrofuran | recrystall'n | 106-110 |
| 82 | 2-(p-methoxyphenylsulfonyl)ethyltrimethyl- | H | 1 | $-SO_2-\langle\bigcirc\rangle-OCH_3$ | tetrahydrofuran | recrystall'n | 35.5-39 |
| 83 | 2-(p-bromophenylsulfonyl)ethyltrimethyl- | H | 1 | $-SO_2-\langle\bigcirc\rangle-Br$ | tetrahydrofuran | recrystall'n | 84.5-86.5 |
| 84 | 2-(p-fluorophenylsulfonyl)ethyltrimethyl | H | 1 | $-SO_2-\langle\bigcirc\rangle-F$ | tetrahydrofuran | recrystall'n | 65-66.5 |
| 85 | 2-(3,4-dichlorophenylsulfonyl)ethyltrimethyl- | H | 1 | $-SO_2-\langle\bigcirc\rangle-Cl$ with Cl | toluene | recrystall'n | 102.2-103.5 |
| 86 | 2-(2-naphthylsulfonyl)ethyltrimethyl- | H | 1 | $-SO_2-\text{naphthyl}$ | tetrahydrofuran | recrystall'n | 88.5-90.7 |
| 87 | 4-[p-(1,1-dimethylethyl)phenylsulfonyl]butyltrimethyl- | H | 3 | $-SO_2-\langle\bigcirc\rangle-C(CH_3)_3$ | none | recrystall'n | 80-81.8 |
| 88 | 6-(p-tolylsulfonyl)hexyltrimethyl | H | 5 | $-SO_2-\langle\bigcirc\rangle-CH_3$ | none | column chromatography | oil |
| 89 | 11-(p-tolylsulfonyl)undecyltrimethyl- | H | 10 | $-SO_2-\langle\bigcirc\rangle-CH_3$ | none | column chromatography | oil |

*branched

Compounds 90-92, and similar compounds in which n=2 or more and X is $-SO_2R_1$, $-OR_7$ or $-SR_{10}$, can be prepared by an alternative method from those shown above, the starting materials being:

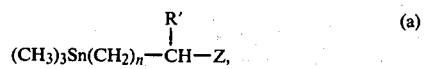
(a)

where Z is chlorine, bromine, or iodine; and
(b) AlkSO$_2$R$_1$, AlkOR$_7$ or AlkSR$_{10}$, where Alk is sodium, potassium, or lithium.

Suitable type (a) starting materials include:

4-bromobutyltrimethylstannane;
3-chloropropyltrimethylstannane;
5-bromopentyltrimethylstannane;
6-chlorohexyltrimethylstannane;
7-bromoheptyltrimethylstannane;
8-iodooctyltrimethylstannane;
9-chlorononyltrimethylstannane;
10-bromodecyltrimethylstannane;
11-bromoundecyltrimethylstannane.

Suitable type (b) starting materials include: AlkSO$_2$R$_1$
sodium benzenesulfinate;

sodium p-toluenesulfinate;
sodium p-ethylbenzenesulfinate;
sodium p-n-propylbenzenesulfinate;
sodium p-i-propylbenzenesulfinate;
sodium p-n-butylbenzenesulfinate;
sodium p-s-butylbenzenesulfinate;
sodium p-t-butylbenzenesulfinate;
sodium p-i-butylbenzenesulfinate;
sodium p-n-amylbenzenesulfinate;
sodium p-t-amylbenzenesulfinate;
sodium p-n-hexylbenzenesulfinate;
sodium p-n-octylbenzenesulfinate;
sodium p-n-nonylbenzenesulfinate;
sodium p-n-decylbenzenesulfinate;
sodium p-n-undecylbenzenesulfinate;
sodium p-n-dodecylbenzenesulfinate;
sodium p-n-tridecylbenzenesulfinate;
sodium p-cyclohexylbenzenesulfinate;
sodium 2,4-dimethylbenzenesulfinate;
sodium 2,5-dimethylbenzenesulfinate;
sodium 2,4-diethylbenzenesulfinate;
potassium 2,5-diisopropylbenzenesulfinate;
potassium 2,4,6-trimethylbenzenesulfinate;
potassium p-methoxybenzenesulfinate;
potassium p-ethoxybenzenesulfinate;
potassium p-butoxybenzenesulfinate;
potassium 2,5-dimethoxybenzenesulfinate;
potassium 3,4-dimethoxybenzenesulfinate;
potassium p-methylthiobenzenesulfinate;
potassium p-butylthiobenzenesulfinate;
potassium 5-chloro-2-methoxybenzenesulfinate;
potassium 2-bromo-4-methoxybenzenesulfinate;
potassium 5-acetamido-2-methoxybenzenesulfinate;
potassium 5-nitro-2-methoxybenzenesulfinate;
potassium 2-methyl-4-methoxybenzenesulfinate;
potassium 2-methyl-5-chlorobenzenesulfinate
potassium p-fluorobenzenesulfinate;
potassium p-bromobenzenesulfinate;
potassium p-chlorobenzenesulfinate;
potassium 2,5-dichlorobenzenesulfinate;
potassium 2,4,5-trichlorobenzenesulfinate;
potassium trifluoromethylbenzenesulfinate;
potassium 3-nitrobenzenesulfinate
potassium 3,5-dichloro-2-hydroxybenzenesulfinate;
potassium p-acetamidobenzenesulfinate;
potassium p-carboxybenzenesulfinate;
potassium p-butoxycarbonylbenzenesulfinate;
potassium p-carbamoylbenzenesulfinate;
potassium p-cyanobenzenesulfinate;
potassium p-acetylbenzenesulfinate;
potassium 2-naphthalenesulfinate;
potassium p-phenylbenzenesulfinate;
potassium methanesulfinate;
potassium ethanesulfinate;
potassium 1-propanesulfinate;
potassium 2-propanesulfinate;
potassium 2-butanesulfinate;
potassium 2-pentanesulfinate;
potassium cyclohexanesulfinate;
lithium 1-octanesulfinate;
lithium 1-dodecanesulfinate;
lithium 1-octadecanesulfinate;
1,2-ethylenebis lithium sulfinate;
1,4-tetramethylenebis lithium sulfinate.

AlkOR$_7$ sodium methoxide;
sodium ethoxide;
sodium n-propoxide;
sodium t-butoxide;
sodium n-heroxide;
sodium 2-ethylhexoxide;
sodium n-decoxide;
sodium n-dodecoxide;
sodium n-eicosoxide;
sodium n-stearyloxide;
sodium phenoxide;
lithium naphthoxide;
lithium p-ethylphenoxide;
lithium p-i-propylphenoxide;
lithium p-n-tridecylphenoxide;
lithium 2,4-dimethylphenoxide;
lithium 2,5-dimethylphenoxide;
lithium 2,4,5-trimethylphenoxide;
lithium p-methoxyphenoxide;
lithium p-n-butoxyphenoxide
lithium 3,4-dimethoxyphenoxide;
lithium p-n-octoxyphenoxide;
potassium p-chlorophenoxide;
potassium p-fluorophenoxide;
potassium p-bromophenoxide;
potassium 2,5-dichlorophenoxide;
potassium 2-methyl-5-chlorophenoxide;
potassium p-acetylphenoxide;
potassium 3-nitrophenoxide;
potassium p-methylthiophenoxide;
potassium 5-nitro-2-methoxyphenoxide;
potassium p-acetylphenoxide;
potassium cyclohexoxide.

AlkSR$_{10}$ sodium methylmercaptide;
sodium ethylmercaptide;
sodium n-propylmercaptide;
sodium i-propylmercaptide;
sodium n-butylmercaptide;
sodium s-butylmercaptide;
sodium t-butylmercaptide;
sodium n-pentylmercaptide;
sodium i-pentylmercaptide;
sodium s-pentylmercaptide;
sodium t-pentylmercaptide;
sodium n-hexylmercaptide;
sodium cyclohexylmercaptide;
sodium 4-methylcyclohexylmercaptide;
sodium n-octylmercaptide;
sodium benzylmercaptide;
sodium p-chlorobenzylmercaptide;
sodium phenylmercaptide;
sodium p-tolylmercaptide;
sodium p-ethylphenylmercaptide;
sodium p-n-propylphenylmercaptide;
sodium p-i-propylphenylmercaptide;
sodium p-n-butylphenylmercaptide;
sodium p-i-butylphenylmercaptide;
sodium p-s-butylphenylmercaptide;
sodium p-t-butylphenylmercaptide;
sodium p-n-pentylphenylmercaptide;
sodium p-t-pentylphenylmercaptide;
sodium p-n-hexylphenylmercaptide;
sodium p-n-heptylphenylmercaptide;
sodium p-n-octylphenylmercaptide;
sodium p-nonylphenylmercaptide;
sodium p-decylphenylmercaptide;

sodium p-dodecylphenylmercaptide;
sodium p-tridecylphenylmercaptide;
sodium p-cyclohexylphenylmercaptide;
sodium 2,4-dimethylphenylmercaptide;
sodium 2,5-dimethylphenylmercaptide;
sodium 2,4-diethylphenylmercaptide;
sodium 2,5-diisopropylphenylmercaptide;
sodium 2,4,6-trimethylphenylmercaptide;
sodium p-methoxyphenylmercaptide;
sodium p-ethoxyphenylmercaptide;
sodium p-butoxyphenylmercaptide;
sodium p-octoxyphenylmercaptide;
sodium 3,4-dimethoxyphenylmercaptide;
sodium p-methylthiophenylmercaptide;
sodium 5-chloro-2-methoxyphenylmercaptide;
sodium 2-chloro-4-methoxyphenylmercaptide;
sodium 3-bromo-4-methoxyphenylmercaptide;
sodium 2-nitro-4-methoxyphenylmercaptide;
sodium 2-methyl-4-methoxyphenylmercaptide;
sodium p-fluorophenylmercaptide;
sodium p-bromophenylmercaptide;
sodium p-chlorophenylmercaptide;
sodium 2,5-dichlorophenylmercaptide;
sodium 3,4-dichlorophenylmercaptide;
sodium 2,4,5-trichlorophenylmercaptide;
sodium trifluoromethylphenylmercaptide;
sodium 3-nitrophenylmercaptide;
sodium p-acetamidophenylmercaptide.

The specific preparative details for Compounds 90-92 are presented below. The reaction times range from 0.5 to 24 hours and suitable reaction temperatures are from 20° to 120° C. The catalyst can be any phase transfer catalyst as shown by E. V. Dehmlow, Chem. Tech. (1975), starting at page 210, which citation is hereby incorporated by reference.

EXAMPLE 9

(Compound 90)

Into a 125 ml single-necked round bottom flask fitted with a teflon coated magnetic stir bar and a reflux condenser was charged 4.45 g of sodium p-toluenesulfinate, 20 ml water, 10 ml toluene, 7 g of 75% 4-bromobutyltrimethylstannane and 0.44 g of tri-n-butylhexadecylphosphonium bromide. The mixture was refluxed for 2.5 hours with rapid stirring. On cooling, the organic phase was separated, dried over anhydrous magnesium sulfate and stripped of solvent on a rotary evaporator. The oil residue was distilled two times through a short path distillation head. The second distillation afforded 3.3 g of 4-(p-tolylsulfonyl)butyltrimethylstannane, b.p. 136°-140° C. ($1 \times 10^{-3}$ mm Hg). The presence of both the sulfonyl and trimethyltin moieties was indicated by strong infrared absorption bands at 1315 cm$^{-1}$, 1300 cm$^{-1}$, 1142 cm$^{-1}$ (—SO$_2$—) and 765 cm$^{-1}$ ([(CH$_3$)$_3$Sn—]. NMR spectroscopy showed the following:

The aromatic protons appeared as two multiplets each centered at 768 Hz and 726 Hz (each having 2 protons); the protons alpha to the sulfonyl group appeared as a complex multiplet centered at 291 Hz (2 protons); the beta and gamma methylene protons appeared as a complex multiplet centered at 157 Hz (4 protons); the p-tolyl methyl group appeared as a singlet at 244 Hz (3 protons); the methylene proton adjacent to the tin atom appeared as a complex multiplet centered at 74 Hz (2 protons); the protons of the trimethyltin group appeared as a singlet, flanked on either side by satellite bands, at −4 Hz from the tetramethylsilane internal standard (9 protons).

Analysis: Calc'd for C$_{14}$H$_{24}$O$_2$SSn (percent): C, 44.83; H, 6.45; S, 8.55; Sn, 31.64. Found: C, 44.98; H, 6.61; S, 8.46; Sn, 31.65.

EXAMPLE 10

(Compound 91)

Into a 100 ml single-necked round bottom flask fitted with a teflon coated magnetic stir bar and a reflux condenser was charged 7.68 g of a 1:1 mixture of 4-bromobutyltrimethylstannane and 4-chlorobutyltrimethylstannane, 15 ml of toluene, 5 g of p-t-butylthiophenol, 1.2 g of sodium hydroxide, 20 ml water and 0.44 g of tri-n-butylhexadecylphosphonium bromide. The mixture was refluxed for one-half hour. On cooling, the phases were separated and the water layer extracted with toluene. The organic phase was combined with the extract and washed once with water and dried over anhydrous magnesium sulfate. Solvent was stripped on a rotary evaporator. The product was distilled through a short-path distillation head giving 7.36 g of liquid, 4-(p-t-butylphenylthio)butyltrimethylstannane, b.p. 116°-121° C. ($1 \times 10^{-3}$ mm). The presence of the trimethyltin moiety was indicated by a strong infrared absorption band at 760 cm$^{-1}$. NMR spectroscopy showed the following:

The aromatic protons appeared as a singlet at 717 Hz (4 protons); the protons alpha to the thio group appeared as a multiplet centered at 282 Hz (2 protons); the beta and gamma methylene protons appeared as a multiplet centered at 160 Hz (4 protons); the methyl protons of the t-butyl group appeared as a singlet at 130 Hz (9 protons); the methylene protons adjacent to the tin atom appeared as a complex multiplet centered at 91 Hz (2 protons); the protons of the trimethyltin group appeared as a singlet flanked on either side by satellite bands at 3 Hz (9 protons) from the tetramethylsilane internal standard.

Analysis: Calc'd for C$_{17}$H$_{30}$SSn (percent): C, 53.01; H, 7.85; S, 8.32; Sn, 30.81. Found: C, 53.28; H, 8.24; S, 8.28; Sn, 29.98.

EXAMPLE 11

(Compound 92)

In the manner described for Compound #91, a mixture of 10.57 g. of 75% 4-bromobutyltrimethylstannane, 10 ml of toluene, 2.98 g of thiophenol, 1.08 g of sodium hydroxide, 20 ml of water and 0.44 g of tri-n-butylhexadecylphosphonium bromide were heated at 40° C. for one-half hour. The crude product was distilled through a short path head giving 6.14 g of a liquid, 4-(phenylthio)butyltrimethylstannane, b.p. 95°-97° C. (0.02 mm). The presence of the trimethyltin moiety was indicated by a strong infrared absorption band at 760 cm$^{-1}$. NMR spectroscopy showed the following:

The aromatic protons appeared as a complex multiplet centered at 713 Hz (5 protons); the protons alpha to the thio group appeared as a triplet centered at 284 Hz (2 protons); the beta and gamma protons appeared as a complex multiplet centered at 160 Hz (4 protons); the methylene protons adjacent to the tin atom appeared as a complex multiplet centered at 89 Hz (2 protons); the protons of the trimethyltin group appeared as a singlet flanked on either side by satellite bands at 4 Hz (9 protons) from the tetramethylsilane internal standard.

Analysis: Calc'd for $C_{13}H_{22}SSn$ (percent): C, 47.44; H, 6.74; S, 9.74; Sn, 36.07. Found: C, 47.46; H, 6.77; S, 9.29; Sn, 35.43.

EXAMPLE 12

THe organotin compounds of this invention were tested as insecticides and herbicides according to the following procedures:

A. Mosquito Larvae Test

Formulations were prepared by dissolving 30 mg of organotin compound of the invention in 10 ml of acetone. This solution was then diluted to 1 ppm with water. Two 25-ml aliquots were placed in test tubes to which were added 10 to 25 fourth instar larvae of the yellow fever mosquito, *Aedes aegypti* (Linnaeus). The tubes were held in darkness for 72 hours. At the end of this period the percent control was determined.

B. Aphid Contact Test

Test formulations were prepared for spraying at 1000 ppm (parts per million) concentration by dissolving them in a small amount of acetone and adding a suitable wetting agent. Typically, 0.6 gram of organotin compound was dissolved (or suspended) in 10 ml of acetone, 2 drops of Triton-X100 wetting agent (octylphenoxy polyethoxy ethanol with 9–10 mole percent of polyethylene oxide) were added and this was suspended in 300 ml of water to make a 6000 ppm suspension. An aliquot was then further diluted with distilled water to 1000 ppm concentration of organotin compound.

Eight to ten day old barley seedlings, grown ten plants each in a 12 oz. cup, were infested with corn leaf aphids *Rhopalosiphum maidis* (Fitch), two days prior to treatment. Two pots were treated with each formulation by spraying with a spray atomizer while the plants were rotating on a turntable. Following treatment, the plants were held for 5 days in the greenhouse. At the end of this period, the percent control of the aphids was estimated based on the reduction of the population density as compared to untreated plants used as controls.

C. Tobacco Bud Worm Diet Test

Test formulations were prepared at 1000 ppm as in B, the Aphid Contact Test, above. Two-tenths ml of the diluted formulations was pipetted onto the surface of 5 grams of a synthetic diet mixture held in partially filled cells of a plastic jelly tray. Five cells were treated with each chemical dilution. The diet mixture was a modified Vanderzant diet consisting of wheat germ, soy flour, agar, sugar, salts, vitamins, preservatives and water. The jelly trays had fifty cavities per sheet, each cavity being approximately 2.5×4.0×1.5 cm.

Following treatment, a third or early fourth instar larva of the tobacco bud worm, *Heliothis virescens* (Fabricius), was placed in each cell. The trays were then covered with a plastic film plus a sheet or rigid plastic and were held in an incubator at 80° F.

At the end of one week, the trays were examined and the percent control was determined, adjusted for any natural mortality in the controls by Abbott's formula. The trays were held an additional week and any abnormalities in the development of the survivors was noted.

D. Cotton Boll Weevil Test

Formulations were prepared at 1000 ppm as in B, the Aphid Contact Test, above. Cotton seedlings 12 to 14 days old grown in 12 oz cups were used. Two pots were treated with each formulation by spraying with a spray atomizer while rotating the pots on a turntable. Five adult cotton boll weevils, *Anthonomous grandis* Boheman, were placed in each pot following treatment and were caged by covering the pots with an inverted 16 oz styrofoam cup with small perforations punched in the bottom. The surviving weevils were counted after five days in the greenhouse to determine the percent control, corrected for any natural mortality in the control plants by Abbott's formula. The percent reduction in feeding was estimated by visual comparison of the feeding damage to the treated plants with the control (untreated) plants.

E. Mite Contact Test

The formulations used were prepared at 1000 ppm as in B, the Aphid Contact Test, above.

Cotton in the second primary leaf stage, grown in 12 oz cups under greenhouse conditions at 70°–75° F. was used in this test. One plant (two primary leaves) in one pot was used for each replicate and two replicates were used for each organotin compound tested. A one-inch diameter circle of tree tanglefoot, a sticky, non-toxic preparation, was used to confine the mites to the upper leaf surfaces. Approximately 25 adult two-spotted spider mites, *Tetranychus urticae* Koch, were transferred to each test plant 24 hours prior to treatment.

The infested plants were sprayed with the dispersions using a small spray atomizer to thoroughly drench the foliage. The plants were returned to the greenhouse where they were held for six days. After this period, the plants were examined for adult live mites remaining on the leaves. On an estimation basis and in comparison with the number of living mites on the control plants, the percent control was determined.

F. Mite One-Day Residual Test

Test compounds were prepared as in B, the Aphid Contact Test, above but were further diluted to 500 ppm with water.

Cotton, in the second primary leaf stage grown in twelve ounce cups under greenhouse conditions at 70°–75° F., was used in the test.

One plant (two primary leaves) in one pot was used for each replicate; two replicates were used for each concentration of organotin compound tested.

The plants were sprayed with the dispersions using a small spray atomizer to thoroughly drench the foliage.

One day following treatment, a circle of tree tanglefoot was placed on the upper surface of the treated leaves and adult mites, *Tetranychus urticae* Koch, were transferred into this confinement.

Six days following infestation with mites, the plants were examined for adult live mites remaining on the leaves. On an estimation basis in comparison with the number of living mites on the control plants, the percent control was determined.

G. Abbott's Formula:

$$\text{Adjusted \% mortality} = \frac{\% \text{ alive in check} - \% \text{ alive in treated}}{\% \text{ alive in check}} \times 100$$

The results of the above-described tests are set forth in Table II below wherein the compound numbers correspond to those in Table I above.

TABLE II

| Organotin Compounds as Insecticides | | | | | | |
|---|---|---|---|---|---|---|
| Compound No. | % Control Mosquito Larvae 1 PPM | % Control Aphids 1000 PPM | % Control Tobacco Bud Worm 1000 PPM | % Control Cotton Boll Weevil 1000 PPM | Boll Weevil % Feeding Reduced on Cotton | Mite Contact 1000 PPM | Mite One-Day Residual 500 PPM |
| 1 (and 2) | 100 | 100 | 100 | 100 | 100 | 100 | 100 |
| 3 | 60 | 100 | 100 | 87 | 80 | — | 100 |
| 4 | 98 | 100 | 100 | 56 | — | — | 100 |
| 5 | 0 | 100 | 100 | 100 | — | — | 100 |
| 6 | 80 | 100 | 100 | 85 | — | — | 100 |
| 7 | 75 | 100 | 100 | 71 | — | — | 100 |
| 8 | 100 | 100 | 100 | 100 | 100 | — | 100 |
| 9 | 100 | 100 | * | 100 | 100 | — | 90 |
| 10 | 80 | 0 | 100 | 67 | 90 | — | 25 |
| 11 | 100 | 100 | 100 | 100 | 100 | 100 | — |
| 12 | 95 | 100 | 100 | 67 | 90 | — | 100 |
| 13 | 100 | 100 | 100 | 100 | 94 | 100 | ** |
| 14 | 100 | 100 | 100 | 100 | 95 | — | 100 |
| 15 | 100 | 100 | 100 | 100 | 100 | — | 100 |
| 16 | 15 | 100 | 100 | 56 | 70 | — | 95 |
| 17 | 100 | 95 | 100 | 56 | 80 | — | 80 |
| 18 | 100 | 20 | 100 | 28 | 50 | — | 25 |
| 19 | 100 | 30 | 100 | 56 | 90 | — | 90 |
| 20 | 100 | 0 | 100 | 28 | 40 | — | 50 |
| 21 | 100 | 95 | 100 | 67 | 90 | — | 40 |
| 22 | 100 | 100 | 100 | 100 | 100 | — | 95 |
| 23 | 100 | 100 | 100 | 85 | 95 | — | 100 |
| 24 | 100 | 0 | 100 | 43 | 70 | — | 30 |
| 25 | 100 | 0 | 100 | 100 | 95 | — | 0 |
| 26 | 100 | 30 | 100 | 100 | 95 | — | 25 |
| 27 | 100 | 100 | 100 | 57 | 70 | — | 0 |
| 28 | 100 | 100 | 100 | 100 | 100 | — | 100 |
| 29 | 100 | 100 | 100 | 90 | 100 | — | 100 |
| 30 | 100 | 90 | 100 | 100 | 100 | — | 100 |
| 31 | 100 | 60 | 100 | 30 | 50 | — | 25 |
| 32 | 60 | 100 | 100 | 57 | 90 | — | 90 |
| 33 | 100 | 100 | 100 | 100 | 100 | — | 100 |
| 34 | 100 | 100 | 100 | 44 | 70 | 100 | ** |
| 35 | 100*** | 100 | 100 | 75 | 80 | — | 100 |
| 36 | 100 | 100 | 100 | 100 | 95 | — | 100 |
| 37 | 100 | 100 | 100 | 100 | 100 | — | 100 |
| 38 | 100 | 100 | 100 | 44 | 80 | — | 100 |
| 39 | 100 | 100 | 100 | 75 | 80 | — | 50 |
| 40 | 0 | 100 | 100 | 50 | 70 | — | 100 |
| 41 | 100 | 100 | 100 | 100 | 100 | — | 100 |
| 42 | 0 | 100 | 100 | 63 | 70 | — | 100 |
| 43 | 100 | 0 | 100 | 71 | 90 | — | 0 |
| 44 | 70 | 100 | 100 | 75 | 80 | — | 100 |
| 45 | 100 | 100 | 100 | 100 | 100 | — | 100 |
| 46 | 0 | 100 | 100 | 22 | 70 | 100 | — |
| 47 | 15 | 100 | 100 | 85 | 95 | — | 100 |
| 48 | 100 | 100 | 100 | 29 | 95 | — | 100 |
| 49 | 100 | 100 | 100 | 71 | 90 | — | 100 |
| 50 | 0 | 100 | 100 | 100 | 95 | — | 100 |
| 51 | 100 | 100 | 100 | 85 | 95 | — | 95 |
| 52 | 100 | 100 | 100 | 100 | 100 | — | 100 |
| 53 | 100 | 95 | 100 | 100 | 90 | — | 100 |
| 54 | 100 | 100 | 100 | 57 | 70 | — | 100 |
| 55 | 100 | 100 | 100 | 44 | 70 | — | 50 |
| 56 | 100 | 100 | 100 | 100 | 95 | — | 100 |
| 57 | 100 | 100 | 100 | 89 | 95 | — | 80 |
| 58 | 0 | 97 | 100 | 56 | 80 | 100 | ** |
| 59 | 100 | 30 | 100 | 71 | 80 | — | 0 |
| 60 | 100 | 20 | 100 | 89 | 95 | — | 0 |
| 61 | 100 | 100 | 100 | 22 | 50 | — | 90 |

| Compound No. | % Control Mosquito Larvae 1 PPM | % Control Aphids 1000 PPM | % Control Tobacco Bud Worm 1000 PPM | % Control Cotton Boll Weevil 1000 PPM | Boll Weevil % Feeding Reduced on Cotton | Mite One-Day Residual 500 PPM |
|---|---|---|---|---|---|---|
| 62 | 100 | 95 | 100 | 85 | 90 | 45 |
| 63 | 100 | 100 | 100 | 100 | 90 | 100 |
| 64 | 0 | 100 | 100 | 56 | 80 | 100 |
| 65 | 100 | 75 | 100 | 80 | 100 | 50 |
| 66 | 100 | 100 | 100 | 100 | — | 100 |
| 67 | 100 | 100 | 100 | 88 | 100 | 100 |
| 68 | 100 | 100 | 100 | 88 | 100 | 100 |
| 69 | 100 | 100 | 100 | 78 | 95 | 100 |
| 70 | 100 | 100 | 100 | 100 | 100 | 100 |
| 71 | 100 | 100 | 100 | 90 | 50 | 100 |
| 72 | 100 | 90 | 100 | 100 | 50 | 100 |

TABLE II-continued
Organotin Compounds as Insecticides

| | | | | | | |
|---|---|---|---|---|---|---|
| 73 | 100 | 90 | 100 | 100 | 95 | 100 |
| 74 | 100 | 0 | 100 | 100 | 100 | 100 |
| 75 | 100 | 95 | 100 | 80 | 100 | 100 |
| 76 | 100 | 100 | 100 | 100 | 90 | 100 |
| 77 | 100 | 100 | 100 | 100 | 100 | 100 |
| 78 | 100 | 100 | 100 | 100 | 100 | 100 |
| 79 | 100 | 20 | 100 | 100 | 100 | 100 |
| 80 | 100 | 93 | 100 | 90 | 95 | 100 |
| 81 | 100 | 60 | 100 | 100 | 100 | 100 |
| 82 | 75 | 100 | 100 | 75 | 100 | 100 |
| 83 | 15 | 100 | 100 | 75 | 100 | 100 |
| 84 | 86 | 97 | 100 | 100 | 100 | 100 |
| 85 | 100 | 95 | 100 | 100 | 100 | 100 |
| 86 | 100 | 100 | 100 | 90 | 100 | 100 |
| 87 | 100 | 95 | 100 | 87 | 95 | 100 |
| 88 | 100 | 100 | 100 | 100 | 100 | 100 |
| 89 | 100 | 80 | 60 | 100 | 100 | 100 |
| 90 | 100 | 100 | 100 | 90 | 100 | 100 |
| 91 | 100 | 100 | 100 | 90 | 100 | 100 |
| 92 | 100 | 95 | 100 | 90 | 100 | 90 |

| Comparative Data | % Control Mosquito Larvae 1 PPM | % Control Aphids 1000 PPM | % Control Tobacco Bud Worm 1000 PPM | % Control Cotton Boll Weevil 1000 PPM | Boll Weevil % Feeding Reduced on Cotton | Mite One-Day Residual 500 PPM |
|---|---|---|---|---|---|---|
| Stamm et al. 3,206,489 $(nC_4H_9)_3SnCH_2CH_2-S-\overset{O}{\underset{\|}{C}}CH_3$ 2-Thioacetoxyethyltri-n-butyltin | 55 | 95 | 20 | 40 | 90 | 80 |
| Koopmans et al. 3,031,483 $(CH_3)_3SnO\overset{O}{\underset{\|}{S}}-\text{C}_6\text{H}_4-CH_3$ Trimethyltin p-toluenesulfinate | 0 | 98 | 100 | 100 | 100 | 100 |

*100% Control at 100 ppm; not tested at 1000 ppm.
**100% Control at 100 ppm; not tested at 500 ppm.
***100% Control at 0.001 ppm.

The Stamm et al. compound, for which data are presented at the end of Table II, was prepared in accordance with Example 1 of the Stamm et al. patent. The Koopmans et al. compound, for which data are similarly presented, was prepared as follows.

In a 250 ml Erlenmeyer flask was placed a solution of 5.95 g. (0.033 mole) of

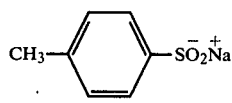

in 50 ml. H₂O. Then 6.6 g. (0.033 mole) (CH₃)₃SnCl in 100 ml. acetone was added dropwise. A white precipitate formed. The reaction mixture was heated to 60° C. for 20 minutes. After stirring overnight, the acetone was removed by evaporation and a white viscous residue separated. The water layer was decanted. The viscous residue was treated with 50 ml. of petroleum ether. A solidified product (8.1 g.), having a m.p. of 98°–102° C., was isolated. Peter M. Slegen, Univ. of North Carolina, Ph.D. thesis 1967, reported m.p. 97°–101° C. for trimethyltin p-toluenesulfinate. The I.R. exhibited strong absorption at 955 cm⁻¹ and 990 cm⁻¹.

As can be seen from the results set forth in Table II above the organotin compounds of the invention exhibit good to superior insecticidal activity for a wide variety of insects, especially in comparison with the two prior art compounds.

In all of the following examples, the numbered compounds correspond to those set forth in Table I above.

EXAMPLE 13
Mite One-Day Residual Test of Organotin Compounds at Different Formulation Concentrations In this example, test formulations were prepared to contain different concentrations of several representative organotin compounds of the invention. The method employed was as follows:

Cotton in the second primary leaf stage, grown in twelve ounce cups under greenhouse conditions at 70°–75° F. was used in this test. One plant (two primary leaves) in one pot was used for each replicate and two replicates were used for each concentration of tin compound tested. Test formulations were prepared by dissolving 50 mgs. of tin compound in one ml of acetone, adding one drop of Emulfor 719, a commercial surface-active dispersing agent (polyoxyethylated vegetable oil) and suspended in 50 ml of water for concentration of 1000 ppm (parts per million). Aliquots of this solution were further diluted with distilled water to concentrations of 100, 20 and 5 ppm. The plants were sprayed with the formulations using a small spray atomizer to thoroughly drench the foliage. One day following treatment, a circle of tree tanglefoot was placed on the upper surfaces of the treated leaves and adult mites, *Tetranychus urticae* Koch, were transferred into this confinement. Counts of these mites were made immediately following transfer and again six days later.

Abbott's formula was used to compensate for check mortality and to obtain the adjusted percent control. The results are shown in Table III below:

TABLE III

| | Mite One-Day Residual Test | | |
|---|---|---|---|
| | | % Control | |
| Compound | 100 PPM | 20 PPM | 5 PPM |
| 1 | 100 | 99 | 63 |
| 14 | 100 | 68 | 49 |
| 23 | 94 | 45 | 44 |
| 41 | 100 | 87 | 57 |

The results above clearly indicate that the selected organotin compounds of the invention exhibit a high degree of effectiveness at different levels of concentration.

EXAMPLE 14

Tobacco Bud Worm—Cotton Test

The test formulations in this example were also prepared to contain different concentrations of representative compounds of the invention which were then tested according to the procedure described below:

Test formulations were prepared by dissolving 50 mg of organotin compound of the invention in one ml of acetone, adding one drop of Emulfor 719, a commercial surface-active dispersing agent (polyoxyethylated vegetable oil) and suspended in 50 ml of water for a concentration of 1000 ppm (parts per million). Aliquots of the solution were further diluted with distilled water to concentrations of 100, 20 and 5 ppm.

Cotton seedlings two weeks old were used. These were grown in 12 ounce cups with two plants in each cup. The diluted formulations were applied to the seedling plants with a spray atomizer and allowed to dry. Three cups were treated with each diluted formulation. A third instar larvae of the tobacco bud worm, *Heliothis virescens* (Fabricius), was placed in each cup and confined by inverting a perforated 16 oz. styrofoam cup over the top. Percent control of the worms was determined after two weeks in the greenhouse.

The results of this test are set forth in Table IV below:

TABLE IV

| | Tobacco Bud Worm on Greenhouse Cotton | | |
|---|---|---|---|
| | | % Control | |
| Compound No. | 100 PPM | 20 PPM | 5 PPM |
| 1 | 100 | 100 | 100 |
| 14 | 100 | 100 | 50 |
| 23 | 66 | 50 | 0 |
| 36 | 100 | 33 | 66 |
| 41 | 100 | 100 | 0 |
| 45 | 100 | 100 | 0 |
| 52 | 100 | 0 | 0 |
| 56 | 66 | 33 | 0 |

As can be seen from the results shown in Table IV above, the organotin compounds of the invention are generally excellent in controlling this type of insect.

EXAMPLE 15

Aphid—Soil Drench Test

This example is similar to Examples 7 and 8 above in that test formulations containing different concentrations of representative organotin compounds were prepared and then tested according to the following procedure:

Test formulations were prepared by dissolving 10 mg of organotin compound of the invention in one ml of acetone plus one drop (about 30 mg) of Emulfor 719, the same surface-active agent identified in Example 9 above, and diluting with water to 100 ml for a concentration of 100 ppm of the test organotin compound in water. Further dilutions were made to 10 ppm and 1 ppm with water.

Barley seedlings eight days old, grown in 12 oz. cups, 10 plants per cup, with a total weight, including the soil, of approximately 440 grams, were used. The seedlings were deliberately infested with corn leaf aphids, *Rhopalosiphum maidis* (Fitch), a day prior to treatment. Twenty-two ml aliquots of the dilute formulations were drenched on the surface of the cups, but not over the infested plant parts. Two cups were treated with each rate. Rates were calculated in pounds per acre based on a weight of 440 gms/cup and assuming an acre of soil seven inches deep weighs two million pounds.

The percent control was determined by observations made one week following treatment. The results are set forth in Table V below wherein "#/A" denotes the calculated pounds per acre.

TABLE V

| | barley Soil Drench | | |
|---|---|---|---|
| Compound | | % Control of Aphids | |
| No. | 10#/A | 1#/A | 0.1#/A |
| 1 | 100 | 93 | 86 |
| 14 | 86 | 30 | 0 |
| 23 | 95 | 86 | 78 |
| 45 | 100 | 99 | 0 |
| 52 | 100 | 80 | 40 |
| 56 | 100 | 97 | 70 |

This test demonstrates that the chemicals of this invention are also effective as systemic insecticides on barley plants in that they absorb sufficient amounts of the organotin compounds of the invention to effectively control aphids.

EXAMPLE 16

Organotin Compounds as Preemergence Herbicides

This example illustrates the use of the organotin compounds of the invention as preemergence herbicides. Six hundred mg of organotin compound was dissolved in 10 ml of an organic solvent (e.g., acetone) to which 30 mg of a commercial emulsifying agent (e.g., isooctyl polyethoxy ethanol, "Triton X100") was added. The solution was diluted to 100 ml with distilled water. Twenty milliliters of this 6000 ppm solution was further diluted to 250 ppm with distilled water. The solution was applied at the rate of 10#/A (pounds per acre) by drenching 46 ml of the 250 ppm solution on the surface of soil compound in 4½ inch plastic pots which had been planted with the following weeds: rough pigweed, *Amaranthus retroflexus* L.: purslane, *Portulaca oleracea* L.; or jimsonweed, *Datura stramonium* L.; tall morningglory, *Ipomea purpurea* (L.) Roth; crabgrass, *Digitaria ischaemum* (Schreb.) Muhl.; barnyardgrass, *Echinochloa crusgalli* (L.) Beauv.; giant foxtail, *Setaria faberi* Herm.; and southern nutsedge, *Cyperus rotundus* L. The percent control of the weeds as compared to untreated weeds used as checks was determined two weeks after treatment. Table VI data below show the efficacy of the compounds of the invention as preemergence herbicides.

TABLE VI

Organotin Compounds as Preemergence Herbicides

| Compound No. | Rate Lb/A | Pigweed | Purslane (p) or Jimsonweed | Wild Morning glory | Crabgrass | Giant Foxtail | Barnyard Grass |
|---|---|---|---|---|---|---|---|
| 1 | 10 | 100 | 100p | 100 | 100 | 100 | 100 |
| 3 | 10 | 100 | 100 | 100 | 100 | 100 | 100 |
| 4 | 10 | 100 | 100 | 100 | 100 | 100 | 100 |
| 5 | 10 | 100 | 100 | 100 | 100 | 100 | 100 |
| 6 | 10 | 100 | 100 | 100 | 100 | 100 | 100 |
| 7 | 10 | 100 | 100 | 100 | 100 | 100 | 100 |
| 8 | 10 | 100 | 100 | 100 | 100 | 100 | 100 |
| 9 | 10 | 100 | 100 | 10 | 15 | 30 | 20 |
| 11 | 10 | 100 | 100p | 100 | 100 | 100 | 100 |
| 12 | 10 | 100 | 100 | 100 | 100 | 100 | 100 |
| 13 | 20 | 100 | 100p | 100 | 100 | 100 | 100 |
| 14 | 10 | 100 | 100 | 98 | 100 | 100 | 80 |
| 15 | 10 | 100 | 100 | 100 | 100 | 100 | 100 |
| 16 | 10 | 100 | 100 | 100 | 100 | 100 | 100 |
| 17 | 10 | 100 | 100 | 50 | 100 | 100 | 100 |
| 18 | 10 | 100 | 100 | 100 | 100 | 100 | 100 |
| 19 | 10 | 100 | 100 | 100 | 100 | 100 | 100 |
| 20 | 10 | 100 | 100 | 100 | 100 | 100 | 100 |
| 21 | 10 | 100 | 100 | 95 | 85 | 60 | 100 |
| 22 | 10 | 100 | 95 | 50 | 95 | 80 | 100 |
| 23 | 10 | 100 | 50p | 65 | 70 | 90 | 80 |
| 24 | 10 | 100 | 100 | 100 | 100 | 100 | 100 |
| 25 | 10 | 100 | 100 | 100 | 100 | 100 | 100 |
| 26 | 10 | 100 | 98 | 0 | 50 | 95 | 0 |
| 27 | 10 | 90 | 80 | 90 | 100 | 100 | 10 |
| 28 | 10 | 0 | 0 | 0 | 0 | 0 | 0 |
| 29 | 10 | 100 | 100 | 35 | 65 | 98 | 100 |
| 30 | 10 | 100 | 0 | 25 | 0 | 98 | 100 |
| 31 | 10 | 100 | 0 | 100 | 90 | 100 | 90 |
| 32 | 10 | 100 | 100 | 100 | 100 | 100 | 100 |
| 33 | 10 | 100 | 100 | 80 | 65 | 98 | 100 |
| 34 | 10 | 100 | 100p | 100 | 100 | 100 | 100 |
| 35 | 10 | 100 | 80 | 20 | 90 | 100 | 60 |
| 36 | 10 | 45 | 0 | 20 | 60 | 60 | 40 |
| 37 | 10 | 100 | 100 | 100 | 100 | 100 | 100 |
| 38 | 10 | 100 | 100 | 98 | 100 | 100 | 100 |
| 39 | 10 | 100 | 100 | 100 | 100 | 100 | 100 |
| 40 | 10 | 100 | 100 | 100 | 100 | 100 | 100 |
| 41 | 10 | 85 | 0 | 0 | 80 | 0 | 0 |
| 42 | 10 | 100 | 100 | 95 | 95 | 100 | 100 |
| 43 | 10 | 65 | 0 | 0 | 0 | 0 | 99 |
| 44 | 10 | 100 | 80 | 20 | 60 | 60 | 60 |
| 45 | 10 | 100 | 90 | 35 | 75 | 0 | 98 |
| 46 | 10 | 100 | 100p | 100 | 100 | 100 | 100 |
| 47 | 10 | 100 | 100 | 90 | 95 | 85 | 85 |
| 48 | 10 | 100 | 100 | 0 | 100 | 100 | 45 |
| 49 | 10 | 100 | 100 | 100 | 100 | 100 | 100 |
| 50 | 10 | 100 | 100 | 100 | 100 | 100 | 100 |
| 51 | 10 | 100 | 100 | 80 | 100 | 100 | 100 |
| 52 | 10. | 100 | 100 | 95 | 100 | 90 | 100 |
| 53 | 10 | 100 | 100 | 98 | 100 | 100 | 100 |
| 54 | 10 | 100 | 100 | 30 | 100 | 100 | 100 |
| 55 | 10 | 100 | 100 | 100 | 100 | 100 | 100 |
| 56 | 10 | 100 | 100 | 30 | 100 | 100 | 100 |
| 57 | 10 | 100 | 100 | 100 | 100 | 100 | 100 |
| 58 | 10 | 100 | 100p | 90 | 100 | 100 | 100 |
| 59 | 10 | 100 | 100 | 100 | 100 | 100 | 100 |
| 61 | 10 | 100 | 0 | 100 | 95 | 70 | 98 |
| 62 | 10 | 100 | 100 | 85 | 95 | 85 | 98 |
| 63 | 10 | 95 | 85 | 0 | 0 | 0 | 0 |

As can be seen from the results set forth in Table VI above, the organotin compounds of the invention are generally excellent as preemergence herbicides for a wide variety of weeds.

EXAMPLE 17

Organotin Compounds as Postemergence Herbicides

This example illustrates the effectiveness of the organotin compounds of the invention as postemergence herbicides. The 6000 ppm solution described in Example 10 above was obtained in the same manner and atomized with a conventional DeVilbiss sprayer wetting the foliage to the drip point. The weeds, which were the same species as described in Example 10 above, were treated six days after emergence. The percent control was evaluated two weeks after treatment. Table VII below shows the results using compounds of the invention as postemergence herbicides.

TABLE VII

Organotin Compounds as Postemergence Herbicides

| Compound No. | Rate PPM | Pigweed | Purslane (p) or Jimsonweed | Wild Morning glory | Crabgrass | Giant Foxtail | Barnyard Grass |
|---|---|---|---|---|---|---|---|
| 1 | 6000 | 100 | 100p | 50 | 50 | 90 | 60 |
| 3 | 6000 | 100 | 90 | 100 | 100 | 100 | 100 |
| 4 | 6000 | 100 | 100 | 100 | 100 | 75 | 100 |
| 5 | 6000 | 100 | 90 | 100 | 100 | 100 | 100 |
| 6 | 6000 | 100 | 100 | 100 | 100 | 100 | 100 |
| 7 | 6000 | 100 | 100 | 100 | 100 | 100 | 100 |
| 8 | 6000 | 100 | 100 | 100 | 100 | 98 | 100 |
| 9 | 6000 | 100 | 15 | 100 | 15 | 40 | 40 |
| 10 | 6000 | 98 | 5 | 15 | 0 | 5 | 10 |
| 11 | 6000 | 100 | 100 | 100 | 100 | 100 | 100 |
| 12 | 6000 | 100 | 100 | 100 | 100 | 100 | 100 |
| 13 | 6000 | 100 | 100p | 100 | 100 | 100 | 100 |
| 14 | 6000 | 98 | 65 | 95 | 15 | 5 | 30 |
| 15 | 6000 | 100 | 100 | 100 | 30 | 35 | 75 |
| 16 | 6000 | 100 | 100 | 100 | 50 | 95 | 98 |
| 17 | 6000 | 100 | 15 | 100 | 65 | 25 | 40 |
| 18 | 6000 | 75 | 15 | 30 | 5 | 0 | 15 |
| 19 | 6000 | 20 | 5 | 25 | 15 | 15 | 15 |
| 20 | 6000 | 15 | 20 | 80 | 10 | 0 | 10 |
| 21 | 6000 | 10 | 0 | 30 | 10 | 5 | 0 |
| 22 | 6000 | 30 | 0 | 75 | 20 | 10 | 5 |
| 23 | 6000 | 100 | 0 | 98 | 5 | 3 | 25 |
| 24 | 6000 | 90 | 25 | 75 | 15 | 0 | 10 |
| 25 | 6000 | 100 | 50p | 25 | 5 | 0 | 90 |
| 26 | 6000 | 15 | 5 | 15 | 5 | 0 | 10 |
| 27 | 6000 | 100 | 0 | 35 | 75 | 60 | 70 |
| 28 | 6000 | 25 | 0 | 35 | 50 | 15 | 10 |
| 29 | 6000 | 100 | 10 | 98 | 95 | 35 | 15 |
| 30 | 6000 | 65 | 5 | 60 | 25 | 5 | 5 |
| 31 | 6000 | 0 | 0 | 0 | 5 | 0 | 0 |
| 32 | 6000 | 100 | 10 | 100 | 65 | 35 | 20 |
| 33 | 6000 | 100 | 0 | 50 | 35 | 5 | 5 |
| 34 | 6000 | 100 | 100p | 100 | 100 | 100 | 100 |
| 35 | 6000 | 95 | 25 | 90 | 60 | 70 | 60 |
| 36 | 6000 | 100 | 25 | 95 | 40 | 50 | 60 |
| 37 | 6000 | 100 | 100 | 100 | 100 | 100 | 100 |
| 38 | 6000 | 100 | 100 | 100 | 100 | 100 | 100 |
| 39 | 6000 | 100 | 30 | 45 | 35 | 5 | 15 |
| 40 | 6000 | 90 | 20 | 40 | 50 | 80 | 80 |
| 41 | 6000 | 100 | 0 | 75 | 0 | 0 | 15 |
| 42 | 6000 | 95 | 20 | 95 | 50 | 80 | 80 |
| 43 | 6000 | 65 | 5 | 10 | 0 | 0 | 0 |
| 44 | 6000 | 95 | 0 | 25 | 20 | 20 | 25 |
| 45 | 6000 | 100 | 5 | 75 | 25 | 75 | 75 |
| 46 | 6000 | 100 | 100p | 100 | 90 | 98 | 85 |
| 47 | 6000 | 100 | 50 | 90 | 50 | 35 | 70 |
| 48 | 6000 | 100 | 0 | 20 | 5 | 5 | 25 |
| 49 | 6000 | 100 | 100 | 100 | 100 | 100 | 100 |
| 50 | 6000 | 100 | 100 | 100 | 98 | 95 | 100 |
| 51 | 6000 | 100 | 100 | 100 | 100 | 100 | 100 |
| 52 | 6000 | 90 | 15 | 0 | 10 | 10 | 10 |
| 53 | 6000 | 100 | 95 | 100 | 95 | 98 | 90 |
| 54 | 6000 | 100 | 100 | 98 | 100 | 90 | 98 |
| 55 | 6000 | 100 | 5 | 95 | 10 | 5 | 30 |
| 56 | 6000 | 100 | 100 | 100 | 100 | 98 | 98 |
| 57 | 6000 | 100 | 100 | 100 | 100 | 100 | 100 |
| 58 | 6000 | 100 | 75p | 85 | 80 | 60 | 70 |
| 59 | 6000 | 90 | 15 | 25 | 5 | 0 | 10 |
| 60 | 6000 | 98 | 10 | 5 | 5 | 5 | 10 |
| 61 | 6000 | 100 | 0 | 20 | 0 | 0 | 10 |
| 62 | 6000 | 98 | 80 | 75 | 15 | 5 | 35 |
| 63 | 6000 | 100 | 20 | 90 | 80 | 65 | 80 |

The results in Table VII above reveal that the organotin compounds of the invention are also generally excellent as postemergence herbicides for a wide variety of weeds.

As is brought out above in the discussion of prior art under "Background of the Invention", a Peterson sulfonyl compound was reported as being subject to hydrolysis on being exposed to air. The work reported in the following Example serves as confirmation of this conclusion.

EXAMPLE 18

A. The compound subjected to humid air was a typical Peterson compound, phenylsulfonylmethyltrimethylstannane,

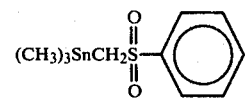

A 5 gal. jar was set on its side on a wooden support and contained a wire mesh screen to support samples in test over a mixture of 152 g of (NH₄)₂SO₄ in 168 g of H₂O. An excess of (NH₄)₂SO₄ in contact with a saturated aqueous solution of (NH₄)₂SO₄ gives 81% humidity in a closed space.[1] The following samples of this Peterson compound were weighed into 40 mm O.D. petri dishes (minus cover) of 8 mm depth and the dishes placed into the humidity chamber, and the chamber was then closed: #15 dish 0.2186 g; #34 dish 0.2006 g. Before the samples were removed from the balance, a solid crust began forming on the surface of the liquid and, inside of ten minutes, covered all of the liquid surface. An odor of a volatile trimethyltin compound was noted. When the samples were placed in the humidity chamber, the samples coated almost all of the surface area inside the dishes. The 5 gal. jar was set on the bench under normal laboratory lighting. The initial temperature inside the chamber was 24.5° C. Over 4 days, the temperature ranged from the initial temperature as a high to a low temperature of 18° C. The #15 sample was removed after 4 days. Under the surface crust, there was an oily solid. The sample was scraped with a spatula into a 2 dram sample vial. The oily solid remaining was washed into the vial with chloroform (about 0.5 to 1 ml). The chloroform was removed under a stream of nitrogen. The #34 sample was removed from the chamber after 7 days. The sample was completely solid and was scraped into a vial. The NMR spectra for both samples showed that, in addition to the aromatic absorptions, there was one singlet due to CH₃ of the hydrolysis product,

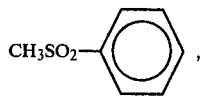

at 307 Hz and a broadened singlet flanked by satellites at 36.5 Hz for (CH₃)₃Sn and a broadened singlet at 191 Hz for the OH. These results indicate the formation of a mixture of trimethyltin hydroxide and methylphenyl sulfone. There was no unreacted starting Peterson compound.

[1] Handbook of Chemistry and Physics, Chem. Rubber Pub. Co., p. 2500 (1960).

B. A corresponding compound of this invention, phenylsulfonylethyltrimethylstannane,

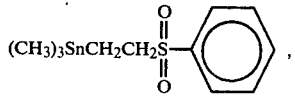

was subjected to similar humidity conditions in the same equipment. The following samples of the indicated compound, purified by column chromatography, were weighed into small petri dish covers and placed in the 81% humidity chamber at a temperature of 27° C.: Dish #15 0.2426 g; Dish #34 0.2020 g. Over the period of the test, the temperature was maintained at room temperature. The #34 sample was removed from the chamber after 4 days and an infrared spectrum was run within several minutes. This showed no additional absorption bands from those of the starting material. The #15 sample was removed from the chamber after 2 weeks. The infrared spectrum of this sample was superimposable with the spectrum of the starting material. No additional absorption bands were present. The NMR spectra for both samples were identical to that for the starting material. It is thus established that the tested compound of this invention is not subject to hydrolysis under the stated conditions.

The following represents an attempt to follow the general procedure of U.S. Pat. No. 3,794,670 of Peterson for the preparation of a compound of this invention, 2-[p-t-butylphenylsulfonyl]ethyltrimethylstannane,

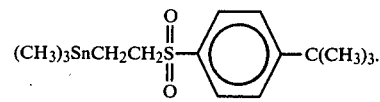

However, the compound obtained is shown to be 1-[p-t-butylphenylsulfonyl]ethyltrimethylstannane,

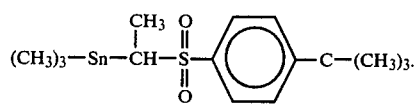

This suffers from the same hydrolysis deficiencies as does the Peterson compound of the preceding Example.

EXAMPLE 19

The equipment utilized was a 500 ml 3-necked round bottom flask fitted with mechanical stirrer, N₂ inlet with Y-tube, 125 ml addition funnel (flame dried and N₂ filled) and ice water bath; for later use: simple distillation take-off, thermometer and oil bath. The materials used were:

(1) 140.0 ml (total volume) reagent benzene distilled to remove water azeotrope.
(2) 18.5 ml (13.1 g, 0.18 mole) diethylamine (dried).
(3) 94.0 ml (0.15 mole) 1.6 molar n-butyllithium in n-hexane.
(4) 29.8 gm (0.15 mole) trimethyltin chloride.
(5) 33.9 gm (0.15 mole) p-t-butylphenylethylsulfone (mol. wt. 226.3).

All syringes used were previously oven dried at 110° C. and cooled under N₂. The diethylamine (via syringe)+50 ml of benzene (via syringe) were introduced into the flask. The butyllithium was placed into the addition funnel (via syringe). The reaction flask was cooled with mechanical stirring using the ice water bath and the butyllithium was added dropwise over a period of 33 minutes. The reaction solution was now milky white. The addition funnel was rinsed with 10 ml of benzene (via syringe) and drained directly into the reaction flask. Into a N₂ flushed 125 ml Erlenmeyer flask the trimethyltin chloride was weighed out and dissolved in 50 ml of benzene (via syringe) and poured into the addition funnel (via syringe). An additional 25 ml benzene was used to rinse the flask, and was then added to the addition funnel. While keeping the reaction mixture at 0°–5° C. with the ice bath, the tin chloride solution was added dropwise over a period of 1 hour. The reaction mixture was then allowed to warm to room temperature with stirring for 1 hour and 10 minutes. The sulfone was weighed out and added directly as a solid, and readily dissolved. The mixture was stirred for ½ hour at room temperature and kept overnight under N₂. The reaction mixture was a milky light tan.

In the morning, the apparatus was adapted for distillation—using an immersion thermometer, reflux thermometer, oil bath thermometer plus joint and condenser and a 300 ml flat bottom 1-neck receiver flask—all under nitrogen.

TABLE VIII

| Elapsed Time | Oil Bath Temperature | Internal Pot Temperature | Reflux Temperature | |
|---|---|---|---|---|
| Start | 54 | 37.5 | 24 (R.T.) | |
| 15 mins. | 69 | 55.0 | 24 | |
| 22 mins | 84 | 64 | 49 ↑ | (Distillate coming over into receiver) |
| 25 mins. | 86 | 66 | 54 | |
| 35 mins. | 83 | 73.5 | 61.5 | |
| 46 mins. | 95.5 | 77 | 70 | (Schlieren effect present in receiver) |
| 1 hr. 5 mins. | 100 | 83 | 72 | (Schlieren effect present in receiver) |
| 1 hr. 45 mins. | 110 | 95 | 73 | |
| 2 hrs. | 117 | 105 | 75.5 | |
| 2 hrs. 15 mins. | 123.5 | 112 | 70 | (Take-off decreasing) |
| 3 hrs. 20 mins. | 125 | 115 | 50.5 | (Ceased. Pot contents cloudy; brown slurry) |
| 3 hrs. 55 mins. | 125 | 115 | 60 | (Stirring slowed; some drops over) |
| 4 hrs. 5 mins. | 125.5 | 115.5 | 49 | (Occasional drops) |
| 4 hrs. 15 mins. | 124.5 | 115.5 | 44 | |
| 4 hrs. 50 mins. | 123 | 113 | 43 | (Start $N_2$ sweep through reaction flask to receiver and refluxed back to 66°. Pot temp. to 111° and distillate coming over.) |
| 5 hrs. 5 mins. | 123 | 113 | 57.5 | (Occasional drops) |
| 5 hrs. 15 mins. | 123.5 | 114 | 51 | (Occasional drops; let cool to R.T. under $N_2$.) |

The distillation apparatus was disassembled when cool. The receiver was kept under $N_2$ with stirring, and cooled down to 0°-5° C. with ice bath. A thick, light brown slurry resulted. 4.0 gms (3.4 cc, 0.04 mole) HCl was added to 200 cc $H_2O$ and the resulting solution was added slowly to the receiver. At first, the pot temperature rose to 30°-35° C. and rapidly subsided. The rest of the HCl solution was added. The ice bath was removed; 2 phases formed; a clear upper $H_2O$ and light brown viscous lower oil layer. 100 cc $CHCl_3$ were added to the pot to dissolve the oil, and the whole was transferred to a 1 liter separatory funnel; 100 ml additional $CHCl_3$ were added. Most of the organic layer was decanted. The remaining organic and $H_2O$ layers were washed twice with $CHCl_3$, the resulting organic layers being decanted. The entire combined organic phase was dried over anhydrous $MgSO_4$ overnight. The whole was vacuum filtered using a 15 cm Buchner filter,--keeping covered and avoiding air suction through the funnel to avoid moisture contact. The slightly turbid filtrate was treated with Darco G 60 at room temperature for about 1.5 hours and gravity filtered (kept covered) into a tared 1 liter, 1-neck round bottom flask, and the $CHCl_3$ was stripped on a Rotovac (Rotovac vented under $N_2$) leaving a clear brown, slightly viscous liquid having crude yield of 46.2 gms.

TLC (thin layer chromatography) on silica gel (Eastman) (9/1 volume ratio cyclohexane / EtOAc) showed two large spots with distances from the origin of 25 mm and 37 mm. The shorter distance spot had the same distance as that for the starting ethylsulfone. The spots were approximately of equal size and intensity when observed under short wave U.V. The oil was subjected to vacuum distillation through a short path head using a single 50 ml receiver. An oil was collected between 120°-154° C. at 0.06-0.12 mm Hg. The pot temperature ranged between 150° and 200° C. There appeared to be no separation points using this short path. The oil distillate formed some solid which was isolated by decantation of the oil and pressing the solid on filter paper: 3.86 g. The solid was recrystallized from petroleum ether, m.p. 43°-65°. TLC of this material showed 2 spots the same as the crude product. The distillate oil was redistilled through a microware, vacuum jacketed Vigreaux column. Cut #1: b.p. 48°-112.5° ($2.5-3 \times 10^{-3}$ mm). TLC showed a large spot (starting sulfone) and a faint spot for product. Cut #2: b.p. 108°-136° ($2-8 \times 10^{-3}$ mm). TLC showed a large spot for starting material and a smaller one for product. Cut #3: b.p. 140°-145° (.01 mm) showed the major component as product (faster moving component) and a smaller spot for starting sulfone. Cuts 1 and 2 were discarded as they had very little product. All three cuts were solids. Cut #3 weighed 5.6 g.

The solid from Cut #3 was taken into boiling petroleum ether and filtered to remove cloudiness. The solution was concentrated to about 25 ml and cooled in an ice-water mixture. The solid was pressure filtered under nitrogen to give 2.78 g of white solid, m.p. 78°-81° C. The solid was recrystallized from petroleum ether (about 10-15 ml) (cooled to −15° C.). The solid was filtered with a positive pressure of nitrogen to give 2.21 g of a white crystalline solid, m.p. 79.5°-81.5° C.

The nuclear magnetic spectrum showed that there is a typical 1,4-disubstituted aromatic pattern with a relative intensity of 4 protons, comprising a band centered at 7.75 δ due to the two protons ortho to the $SO_2$ group and its mirror image centered at 7.47 δ due to the two protons ortho to the tertiary butyl group. A quartet of bands centered at 2.84 δ, relative intensity of one proton, is due to the methine proton. The tertiarybutyl and the single methyl resonances overlap to form a band of relative intensity of 12 protons, the tertiarybutyl resonance appearing as a singlet centered at 1.35 δ and the methyl resonance appearing as a doublet centered at 1.29 δ. There is a singlet at 0.37 δ (37 Hz) flanked by two small satellite doublets with a total relative intensity of 9 protons. This band is due to the trimethyltin group. The two sets of satellite doublets are due to the coupling of the three methyl groups to the two isotopes of Sn-$Sn^{117}$ and $Sn^{119}$- with a nuclear spin of ½. Thus, the structure as presented in the paragraph preceding this Example is confirmed.

The comparative data in the following table (Table IX) were obtained on Compound 13 of this invention, a Peterson compound (trimethylphenylsulfonylmethylstannane) and the Peterson hydrolysis product referred to above (trimethyltin hydroxide). The Peterson compound was prepared in accordance with Example 1 of U.S. Pat. No. 3,794,670, except that an equivalent amount of trimethyltin chloride was used instead of trimethyltin bromide. The trimethyltin hydroxide was prepared by the method set forth by J. G. A. Luijten, Rec. trav. chim. 82, 1179 (1963).

The mite one-day residual test differed as follows from that set forth in Example 13. The plants were held in a growth chamber maintained at 85° F., and were exposed to high intensity fluorescent lights for 14 hour days. The recorded observations were made 3 days after loading the mites.

The 3-day tobacco bud worm test on cotton differed as follows from that set forth in Example 14. The plants used were 3 weeks old, and were covered with cheesecloth during the test. Six replicates were used for each test compound, with 1 worm per plant. The recorded observations were made 3 days after the spray application. In both of these tests, the solutions were made in terms of millimoles/liter so that the results would be strictly comparable, since the compounds are of different molecular weights.

TABLE IX

| | Mite One-Day Residual % Control (millimoles/liter) | | | Tobacco Bud Worm | | | | | |
|---|---|---|---|---|---|---|---|---|---|
| | | | | % Control (millimoles/liter) | | | % Feeding Reduced (millimoles/liter) | | |
| | 0.6 | 0.3 | 0.15 | 0.6 | 0.3 | 0.15 | 0.6 | 0.3 | 0.15 |
| Compound 13: (CH$_3$)$_3$SnCH$_2$CH$_2$—S(O)$_2$—C$_6$H$_5$ | 98.4 | 100 | 73 | 100 | 83 | 83 | 98 | 92 | 88 |
| (CH$_3$)$_3$SnCH$_2$—S(O)$_2$—C$_6$H$_5$ | 44 | 14 | 18 | 66 | 0 | 40 | 90 | 52 | 73 |
| (CH$_3$)$_3$SnOH | 9 | 34 | 7 | 66 | 16 | 16 | 81 | 69 | 50 |

The decided superiority of the compound of this invention over the closest comparable Peterson compound and over the hydrolysis product of the latter is readily apparent.

While the invention has been described with particularity and in some detail, it should be understood that it is susceptible to various changes and modifications that will occur to those skilled in the art without departing from the scope of the spirit of the invention.

What is claimed is:

1. A tetrasubstituted organotin compound having the general formula $$(CH_3)_3Sn(CH_2)_n-\underset{\underset{R'}{|}}{CH}-X$$

wherein:

R' is hydrogen, hydroxyl, methyl or ethoxy;
X is
(a) —SO$_2$R$_1$, R' being hydrogen, and wherein R$_1$ is a straight chain or branched alkyl having 1 to 18 carbon atoms, cyclohexyl, benzyl, phenyl or phenyl substituted with one or more groups which may be the same or different and which may be alkoxy having 1 to 8 carbon atoms, phenoxy, alkylthio having 1 to 8 carbon atoms, halogen, nitro, acetyl, acetamido, carboxy, alkoxycarbonyl, carbamoyl, cyano, hydroxy, trifluoromethyl, benzyl, naphthyl or norbornyl; naphthyl, biphenylyl, —R$_2$Sn(CH$_3$)$_3$ wherein R$_2$ is polymethylene having from 2 to 11 carbon atoms, —R$_4$SO$_2$R$_5$Sn(CH$_3$)$_3$ wherein R$_4$ is ethylene and R$_5$ is as defined for R$_2$ above;

(b) —OR$_7$, R' being hydrogen, and wherein R$_7$ is a straight chain or branched alkyl having 8 to 16 carbon atoms, aryl, alkoxyaryl, alkaryl, haloaryl, N,N-dialkylminoalkyl, —R$_8$Sn(CH$_3$)$_3$ wherein R$_8$ is alkylene having 2 to 11 carbon atoms, cycloaliphatic having 4 to 6 carbon atoms;

(c) —SR$_{10}$, R' being hydrogen, and wherein R$_{10}$ is an alkyl having 1 to 16 carbon atoms, chlorophenyl, or R$_2$Sn(CH$_3$)$_3$;

(d) —COR$_{11}$, R' being hydrogen, and wherein R$_{11}$ is —NHR$_{12}$ wherein R$_{12}$ is a straight chain or branched alkyl having 1 to 12 carbon atoms or aryl; —NHCH$_2$OH; —NHNH$_2$; —NHCH$_2$NHCOR$_2$Sn(CH$_3$)$_3$; —OR$_{13}$ wherein R$_{13}$ is a straight chain or branched alkyl having 12 carbon atoms; —(CH$_2$)$_m$OH, wherein m is an integer from 2 to 4; —(CH$_2$)$_p$N(R$_{14}$)$_2$ wherein p is an integer from 2 to 4 and R$_{14}$ is a straight chain or branched alkyl having 1 to 5 carbon atoms; —(CH$_2$)$_q$OCOR$_2$Sn(CH$_3$)$_3$ wherein q is as defined for p above; —(CH$_2$)$_s$N(CH$_3$)$_3$I wherein s is as defined for p above;

(e) —NHCONH$_2$, R' being hydrogen;

(f) —NHCSNH$_2$, R' being hydrogen;

(g) —OCOR$_{17}$, R' being hydrogen, and wherein R$_{17}$ is —NHR$_{18}$ wherein R$_{18}$ is a straight chain or branched alkyl having 1 to 5 carbon atoms; and —O(CH$_2$)$_t$Sn(CH$_3$)$_3$ wherein t is from 2 to 11;

(h) —PO(OR$_{20}$)$_2$, R' being hydrogen or ethoxy, and wherein R$_{20}$ is a straight chain or branched alkyl having 1 to 5 carbon atoms;

(i) —Si(OR$_{21}$)$_3$, R' being hydrogen, and wherein R$_{21}$ is a straight chain or branched alkyl having 1 to 5 carbon atoms;

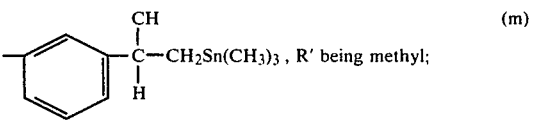  (m)

R' being methyl;

and
n is an integer from 1 to 10.

2. A tetrasubstituted organotin compound having the general formula

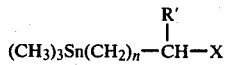

wherein:
R' is hydrogen;
X is —$SO_2R_1$, wherein $R_1$ is a straight chain or branched alkyl having 1 to 18 carbon atoms, cyclohexyl, benzyl, phenyl or phenyl substituted with one of more groups which may be the same or different and which may be alkoxy having 1 to 8 carbon atoms, phenoxy, alkylthio having 1 to 8 carbon atoms, halogen, nitro, acetyl, acetamido, carboxy, alkoxycarbonyl, carbamoyl, cyano, hydroxy, trifluoromethyl, benzyl, naphthyl or norbornyl; naphthyl, biphenylyl, —$R_2Sn(CH_3)_3$ wherein $R_2$ is polymethylene having from 2 to 11 carbon atoms, —$R_4SO_2R_5Sn(CH_3)_3$ wherein $R_4$ is ethylene and $R_5$ is as defined for $R_2$ above; and
n is an integer from 1 to 10.

3. The compound of claim 2 wherein said compound is 2,2'-sulfonylbisethyltrimethylstannane.

4. The compound of claim 1 wherein said compound is 2-dodecoxyethyltrimethylstannane.

5. The compound of claim 1 wherein said compound is N,N'-methylenebis(2-carbamoylethyltrimethylstannane).

6. The compound of claim 1 wherein said compound is 3,3'-(carbonyldioxy)bispropyltrimethylstannane.

7. The compound of claim 1 wherein said compound is 2,2'-(ethylenedioxydicarbonyl)bisethyltrimethylstannane.

8. The compound of claim 2 wherein said compound is trimethyl-2-(n-octylsulfonyl)ethylstannane.

9. The compound of claim 2 wherein said compound is 2-(cyclohexylsulfonyl)ethyltrimethylstannane.

10. The compound of claim 2 wherein said compound is 2-(p-chlorophenylsulfonyl)ethyltrimethylstannane.

11. The compound of claim 2 wherein said compound is 2-(n-dodecylsulfonyl)ethyltrimethylstannane.

12. The compound of claim 2 wherein said compound is trimethyl-2-(phenylsulfonyl)ethylstannane.

13. A tetrasubstituted organotin compound having the general formula

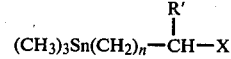

wherein R' is hydrogen and X is —$SO_2R_1$ wherein $R_1$ is a straight chain or branched alkyl having 1 to 18 carbon atoms, cyclopentyl, cyclohexyl, benzyl, phenyl, alkoxyphenyl having 1 to 3 carbon atoms in the alkoxy group, phenoxyphenyl, bicyclo[2.2.1]heptylphenyl, halophenyl, —$R_2Sn(CH_3)_3$ wherein $R_2$ is polymethylene having 2 to 11 carbon atoms or —$R_4SO_2R_5Sn(CH_3)_3$ wherein $R_4$ is ethylene and $R_5$ is as defined for $R_2$ above, and n is an integer from 1 to 10.

14. The compound of claim 13 wherein said compound is 2-(p-bicyclo[2.2.1]hept-2-ylphenylsulfonyl)ethyltrimethylstannane.

* * * * *